(12) United States Patent
Wadhwa et al.

(10) Patent No.: US 12,651,650 B2
(45) Date of Patent: *Jun. 9, 2026

(54) SYSTEM AND METHOD FOR ANALYZING SPECTRAL DATA USING ARTIFICIAL INTELLIGENCE

(71) Applicant: Vionix Biosciences Inc., Belmont, CA (US)

(72) Inventors: Vivek Wadhwa, Belmont, CA (US); Purshotam Rajani, Clayton, NC (US)

(73) Assignee: Vionix Biosciences Inc., Belmont, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/347,104

(22) Filed: Oct. 1, 2025

(65) Prior Publication Data

US 2026/0024624 A1      Jan. 22, 2026

Related U.S. Application Data

(63) Continuation-in-part of application No. 18/828,382, filed on Sep. 9, 2024, now Pat. No. 12,437,842.

(60) Provisional application No. 63/870,459, filed on Aug. 26, 2025, provisional application No. 63/870,464, filed on Aug. 26, 2025, provisional application No. 63/855,046, filed on Jul. 31, 2025, provisional application No. 63/854,206, filed on Jul. 30, 2025, provisional application No. 63/541,177, filed on Sep. 28, 2023.

(51) Int. Cl.
    *G16C 20/20*       (2019.01)
    *G16B 40/10*       (2019.01)
(52) U.S. Cl.
    CPC ............ *G16C 20/20* (2019.02); *G16B 40/10* (2019.02)
(58) Field of Classification Search
    None
    See application file for complete search history.

(56) References Cited

U.S. PATENT DOCUMENTS

| | | |
|---|---|---|
| 10,209,178 B2 | 2/2019 | Carvalho Sousa et al. |
| 10,914,683 B2 | 2/2021 | Mahadevan-Jansen et al. |
| 11,002,681 B2 | 5/2021 | Umapathy et al. |
| 11,079,279 B2 | 8/2021 | Pyun et al. |
| 11,337,643 B2 | 5/2022 | Fan et al. |
| 11,650,195 B2 | 5/2023 | Kaditz et al. |
| 11,698,370 B2 | 7/2023 | Goldman et al. |
| 12,055,495 B2 | 8/2024 | Guadiuso et al. |
| 2018/0098726 A1 | 4/2018 | Pyun et al. |
| 2021/0020276 A1 | 1/2021 | Da Costa Martins |
| 2021/0149361 A1 | 5/2021 | Jungbauer et al. |
| 2021/0231597 A1 | 7/2021 | Emokpae et al. |
| 2022/0203407 A1 | 6/2022 | Kumar et al. |
| 2022/0268751 A1 | 8/2022 | Farkas et al. |
| 2022/0412892 A1 | 12/2022 | Xie et al. |
| 2023/0034263 A1 | 2/2023 | Zhao et al. |
| 2023/0222654 A1 | 7/2023 | Fan et al. |
| 2025/0111900 A1 | 4/2025 | Wadhwa |

FOREIGN PATENT DOCUMENTS

| | | |
|---|---|---|
| WO | 2025003926 A1 | 1/2025 |

OTHER PUBLICATIONS

Arabi et al. AMB Express (2023) vol. 13, No. 61, 12 pages, doi: 10.1186/s13568-023-01569-0.
Bagcioglu et al. Front. Microbiol. (2019) vol. 10, No. 902, 10 pages, doi: 10.3389/fmicb.2019.00902.
Gaudiuso et al. Spectrochimica Acta Part B: Atomic Spectroscopy (2020) vol. 171, 15 pages, doi: 10.1016/j.sab.2020.105931.
Pokrajac et al. Applied Spectroscopy (2014) vol. 68, No. 9, 9 pages, doi: 10.1366/14-07488.
Wang et al. Analytica Chimica Acta (2021) vol. 1179, 11 pages, doi: 10.1016/j.aca.2021.338822.
Murtaza et al. Computer Science Review (2023) vol. 48:40 pages.
Outeiral et al. (WI REs Com put. Mol. Sci. (2021) vol. 11 :23 pages).
Zitnik et al. (Information Fusion (2019) vol. 50:71-91).

*Primary Examiner* — Lori A. Clow
(74) *Attorney, Agent, or Firm* — Neo IP

(57) ABSTRACT

A system provides for an ability to automatically identify one or more chemical components of a sample, based on analysis of spectral data by at least one artificial intelligence module. The artificial intelligence module is able to be trained on a plurality of spectral data samples having known concentrations of individual chemicals and elements. The system is further operable to calculate the correlations between spectral data samples of varying concentrations and predict the concentration of the one or more chemical components of the sample.

20 Claims, 17 Drawing Sheets
(14 of 17 Drawing Sheet(s) Filed in Color)

MBGWATER WITH DIFFERENT TEMPERATURE / PRESSURE & PLASMA POWER CONDITIONS

Relative intensity [arbitrary units] vs wavelength [nm].

NORMALIZED BIDISTILLED VS MBG WATER COMPARISON

Relative intensity [per unit normalized] vs wavelength [nm].

SODIUM DOUBLET DLINES AT 588.9950 AND 589.5924 [nm]
DIFFERENT PRESSURE / PLASMA POWER & CONCENTRATION CONDITIONS

Relative intensity [arbitrary units] vs wavelength [nm]
(NaCl solution Zoomed @589 nm).

Comparison of most representative signals of:
dATP, dCTP, dGTP, dTTP, Water Baseline Relative intensity [arbitrary units] vs wavelength [nm].

Relative intensity [arbitrary units] vs wavelength [nm] (zoom into 300 ~ 400 nm).

Relative intensity [arbitrary units] vs wavelength [nm] (zoom into 350 ~ 650 nm).

ACETONE AND ETHANOL DELTAS
(SUBSTRACTING MOL BIO WATER SPECTRA AS ZERO BASELINE)

Relative intensity [arbitrary units] vs wavelength [nm] (zoom into 350 ~ 650 nm).

Relative intensity [arbitrary units] vs wavelength [nm] (zoom into 350 ~ 650 nm).
Normalized @ 482 [nm] peak for pattern comparison.

Relative intensity [arbitrary units] vs wavelength [nm] (zoom into 465 ~ 500 nm).
Normalized @ 482 [nm] peak for pattern comparison.
Peak at 485 - 486 [nm] appears only in ethanol.

SYSTEM AND METHOD FOR ANALYZING SPECTRAL DATA USING ARTIFICIAL INTELLIGENCE

CROSS-REFERENCE TO RELATED APPLICATIONS

This application is related to and claims priority from the following US patents and patent applications: this application is a continuation-in-part of U.S. patent application Ser. No. 18/828,382, filed Sep. 9, 2024, which claims priority from and the benefit of U.S. Provisional Patent Application No. 63/541,177, filed Sep. 28, 2023. This application further claims priority from and the benefit of U.S. Provisional Patent Application No. 63/854,206, filed Jul. 30, 2025, U.S. Provisional Patent Application No. 63/855,046, filed Jul. 31, 2025, U.S. Provisional Patent Application No. 63/870,459, filed Aug. 26, 2025, and U.S. Provisional Patent Application No. 63/870,464, filed Aug. 26, 2025. Each of the above documents is incorporated herein by reference in its entirety.

BACKGROUND OF THE INVENTION

1. Field of the Invention

The present invention relates to spectroscopic analysis techniques, and more specifically to artificial intelligence-based spectroscopic analysis for multi-element and multi-macromolecule systems in analytes.

2. Description of the Prior Art

It is generally known in the prior art to provide spectroscopic analysis for various substances in order to determine a chemical composition of those samples. Furthermore, it is known to provide artificial intelligence analysis techniques for analyzing results of techniques such as mass spectrometry.

Prior art patent documents include the following:

US Patent Pub. No. 2021/0231597 for Fluid property sensor and fluid particle sensor by inventors Emokpae et al., filed Jan. 22, 2021 and published Jul. 29, 2021, discloses a method, system and apparatus for sensing fluids. A fluid sensor is configured to analyze a fluid utilizing impedance spectroscopy. Capacitive impedance of fluids is sensed and measured. Inductive impedance of suspended particles in fluids is measured. An electrochemical fingerprint of the properties of the fluid or of the particles within the fluid is generated. Fluid analytics data is generated from sensor signal data of the fluids under test. Trainable artificial intelligence algorithms are used to generate fluid analytics data.

U.S. Pat. No. 11,698,370 for Home toilet system for monitoring urine components in real time while urination by inventors Goldman et al., filed Sep. 29, 2021 and issued Jul. 11, 2023, discloses a system for urine sample analysis, where the system may include one or more transmitters for transmitting radiation; one or more sensors that are configured to receive received radiation that passed through the urine sample and to generate detection signals indicative of an intensity of the received radiation at multiple frequencies; detaching elements that are configured to detach the one or more transmitters and the one or more sensors to a toilet bowl; and a processor that is configured to participate in the urine sample analysis for determining a content of the urine sample based on the detection signals.

US Patent Pub. No. 2023/0034263 for Compositions and methods for spatial profiling of biological materials using time-resolved luminescence measurements by inventors Zhao et al., filed Nov. 19, 2020 and published Feb. 2, 2023, discloses compositions, including products of manufacture and kits, and methods, for in situ spatial profiling of biological materials such as DNA, RNA and protein in cells, tissues, and organisms for investigating biology and for conducting biomarker/drug discovery and development, and for clinical pathology and diagnosis. In alternative embodiments, provided are compositions, including products of manufacture and kits, and methods, for spatially determining, visualizing or quantifying target biological materials comprising in situ staining of a biological sample with one or a plurality of probes that are labeled with light-emitting moieties that exhibit or are encoded with distinct luminescence lifetime (and, optionally, spectrum) characteristics; followed by time-resolved luminescence imaging, measurement and analysis.

US Patent Pub. No. 2022/0268751 for Apparatus and method for multimode analytical sensing of items such as food by inventors Farkas et al., filed Feb. 25, 2022 and published Aug. 25, 2022, discloses a multimode biological sample inspection apparatus and method. The apparatus includes an illumination hardware arrangement comprising transmission and sensing hardware configured to inspect a biological sample using at least two modes from a group comprising a fluorescence imaging mode, a reflectance imaging mode, a scattering imaging mode, and a Raman imaging mode, and processing hardware configured to operate the illumination hardware arrangement according to a protocol comprising inspection settings of the at least two modes. The processing hardware receives scan results from the illumination hardware arrangement and identifies attributes of the biological sample by constructing a multidimensional dataset comprising at least one spatial dimension and at least one spectral dimension from the scan results and analyzing the multidimensional dataset. The processing hardware is configured to employ the attributes of at least one biological sample and alter the protocol.

U.S. Pat. No. 10,209,178 for Optical system for parameter characterization of an element of body fluid or tissue by inventors Carvalho Sousa et al., filed Jan. 31, 2014 and issued Feb. 19, 2019, discloses a biophotonic device for the point-of-care, real-time, non-invasive determination of parameters with diagnostic relevance, in particular an optical system for parameter characterization of an element of body fluid or tissue comprising an optical device which comprises: a light source for emitting light onto the element; and a spectrometer for recording the spectrum of light from the element, said light from the element being of transmittance, reflectance or Raman scattering of the emitted light by said element; the optical system further comprising a data processing module configured to: convert the recorded spectrum by a conversion matrix into a standardized spectrum, wherein said conversion matrix has been obtained by calibrating the optical system spectrum response against a spectrum reference; pre-process the converted spectrum; correlate, for parameter quantification, the converted pre-processed spectrum with pre-obtained spectral bands for each parameter; said spectrum being contained within uv-vis-nir wavelengths. Also methods of operating said system.

U.S. Pat. No. 11,650,195 for Iterative medical testing of biological samples by inventors Kaditz et al., filed Sep. 26, 2018 and issued May 16, 2023, discloses a system performing one or more magnetic resonance (MR) measurements on at least a portion of a biological life form. Moreover, the system quantitatively simulates an MR response of at least the portion of the biological life form, and compares the one or more MR measurements and the quantitative simulation to obtain a first test result. Next, the system determines one or more additional medical tests to perform. In response, the system accesses the biological sample in storage, and performs the one or more additional medical tests on at least a second portion of the biological sample to obtain one or more additional test results. Furthermore, the system computes a second test result based at least in part on the first test result and the one or more additional test results, where the second test result has an improved accuracy relative to the first test result.

US Patent Pub. No. 2021/0149361 for Real time monitoring of product purification by inventors Jungbauer et al., filed Apr. 4, 2017 and published May 20, 2021, discloses a method and device which allows in real-time the determination of concentration, purity and potency of a biological product during purification and/or concentration processes in order to intervene into the process, either for process control or real time release. The properties of the process stream are continuously monitored by at least two online sensors and with the aid of multivariate statistical analysis so that concentration, purity and potency is determined in real time.

US Patent Pub. No. 2022/0203407 for Sorting based on chemical composition by inventors Jungbauer et al., filed Mar. 16, 2022 and published Jun. 30, 2022, discloses systems and methods for classifying and sorting materials in order to produce a collection of materials that are composed of a particular chemical composition in the aggregate. The system may utilize a vision system and one or more sensor systems, which may implement a machine learning system in order to identify or classify each of the materials. The sorting is then performed as a function of the classifications.

US Patent Pub. No. 2023/0222654 for Machine learning systems and methods for assessment, healing prediction, and treatment of wounds by inventors Fan et al., filed Mar. 2, 2023 and published Jul. 13, 2023, discloses machine learning systems and methods for prediction of wound healing, such as for diabetic foot ulcers or other wounds, and for assessment implementations such as segmentation of images into wound regions and non-wound regions. Systems for assessing or predicting wound healing can include a light detection element configured to collect light of at least a first wavelength reflected from a tissue region including a wound, and one or more processors configured to generate an image based on a signal from the light detection element having pixels depicting the tissue region, determine reflectance intensity values for at least a subset of the pixels, determine one or more quantitative features of the subset of the plurality of pixels based on the reflectance intensity values, and generate a predicted or assessed healing parameter associated with the wound over a predetermined time interval.

U.S. Pat. No. 11,337,643 for Machine learning systems and techniques for multispectral amputation site analysis by inventors Fan et al., filed Aug. 24, 2020 and issued May 24, 2022, discloses certain aspects relating to apparatuses and techniques for non-invasive and non-contact optical imaging that acquire a plurality of images corresponding to both different times and different frequencies. Additionally, alternatives described herein are used with a variety of tissue classification applications including assessing the presence and severity of tissue conditions, such as necrosis and small vessel disease, at a potential or determined amputation site.

SUMMARY OF TIE INVENTION

The present invention relates to spectroscopic analysis techniques, and more specifically to artificial intelligence-based spectroscopic analysis for multi-element and multi-macromolecule systems in analytes.

It is an object of this invention to provide automatic analysis of spectrographic test results to identify chemical compositions of sample analytes, especially fluids, in order to improve speed and accuracy of results.

In one embodiment, the present invention is directed to an artificial intelligence (AI)-based system for automatically identifying molecules in an analyte, including one or more servers configured to receive training data from one or more spectrometers or chemical analysis devices, at least one reactor, and an AI module on the one or more servers configured to automatically develop characteristic profiles for a plurality of elements, compounds, and/or mixtures of two or more elements and/or compounds based on the training data, wherein the training data includes a plurality of measured spectral graphs corresponding with training samples of known elements, compounds, and/or mixtures of two or more elements and/or compounds, wherein the training samples are of varying concentrations, wherein the AI module generates a plurality of correlation coefficients, wherein the correlation coefficients correlate emission intensity and concentration of the training samples, wherein the at least one reactor is operable to generate plasma from the analyte, wherein the one or more servers receives experimental data for the plasma from a testing spectrometer, and wherein the AI module automatically generates a report with indications and concentrations of present identified molecules based on comparison of the experimental data to the characteristic profiles.

In another embodiment, the present invention is directed to an artificial intelligence (AI)-based method for automatically identifying molecules in an analyte, including receiving training data via one or more servers from one or more spectrometers or chemical analysis devices, wherein the training data includes a plurality of measured spectral graphs corresponding with training samples of known elements, compounds, and/or mixtures of two or more elements and/or compounds, at varying concentrations, generating correlation coefficients for the plurality of measured spectral graphs via an AI module, wherein the correlation coefficients correlate emission intensity and the concentrations of the training samples, automatically developing characteristic profiles for a plurality of elements, compounds, and/or mixtures of two or more elements and/or compounds based on the training data via the AI module on the one or more servers, generating plasma from the analyte using at least one reactor, receiving experimental data for the plasma from a testing spectrometer via the one or more servers, and automatically generating a report with indications and concentrations of present identified molecules based on comparison of the experimental data to the characteristic profiles using the AI module.

In yet another embodiment, the present invention is directed to an artificial intelligence (AI)-based system for automatically identifying molecules in a an analyte, including one or more cloud servers configured to receive training data from one or more spectrometers or chemical analysis devices, at least one reactor, and an AI module on the one or more cloud servers configured to automatically develop characteristic profiles for a plurality of elements, compounds, and/or mixtures of two or more elements and/or compounds based on the training data wherein the training data corresponds with training samples of known elements, compounds, and/or mixtures of two or more elements and/or compounds, wherein the training data received from the one or more spectrometers or chemical analysis devices is stored on the one or more cloud servers, wherein the at least one reactor is operable to generate plasma from the analyte, wherein the one or more cloud servers receive experimental data for the plasma from a testing spectrometer, wherein the AI module automatically generates a report with indications of present identified molecules based on comparison of the experimental data to the characteristic profiles, wherein the AI module automatically generates updated characteristic profiles based on a combination of the stored training data and new training data when the new training data is received from the one or more spectrometers or chemical analysis devices, and wherein the AI module automatically generates an updated report with indications of identified molecules based on comparison of the experimental data to the updated characteristic profiles.

In another embodiment, the present invention is directed to methods to analyze functional groups of chemicals in a mixture of compounds and compositions.

These and other aspects of the present invention will become apparent to those skilled in the art after a reading of the following description of the preferred embodiment when considered with the drawings, as they support the claimed invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1:
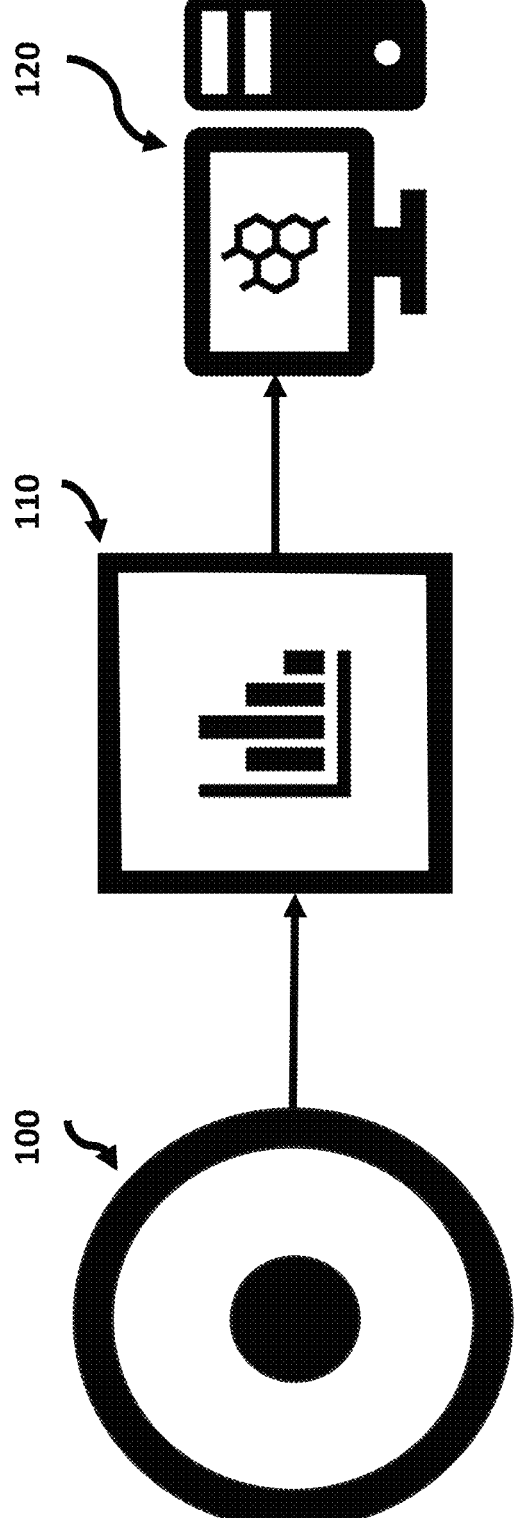
FIG. 1 illustrates an exemplary system of the present invention.

The present invention is generally directed to spectroscopic analysis techniques, and more specifically to artificial intelligence-based spectroscopic analysis for multi-element and multi-macromolecule systems in analytes.

In one embodiment, the present invention is directed to an artificial intelligence (AI)-based system for automatically identifying molecules in an analyte, including one or more servers configured to receive training data from one or more spectrometers or chemical analysis devices, at least one reactor, and an AI module on the one or more servers configured to automatically develop characteristic profiles for a plurality of elements, compounds, and/or mixtures of two or more elements and/or compounds based on the training data, wherein the training data includes a plurality of measured spectral graphs corresponding with training samples of known elements, compounds, and/or mixtures of two or more elements and/or compounds, wherein the training samples are of varying concentrations, wherein the AI module generates a plurality of correlation coefficients, wherein the correlation coefficients correlate emission intensity and concentration of the training samples, wherein the at least one reactor is operable to generate plasma from the analyte, wherein the one or more servers receives experimental data for the plasma from a testing spectrometer, and wherein the AI module automatically generates a report with indications and concentrations of present identified molecules based on comparison of the experimental data to the characteristic profiles.

In another embodiment, the present invention is directed to an artificial intelligence (AI)-based method for automatically identifying molecules in an analyte, including receiving training data via one or more servers from one or more spectrometers or chemical analysis devices, wherein the training data includes a plurality of measured spectral graphs corresponding with training samples of known elements, compounds, and/or mixtures of two or more elements and/or compounds, at varying concentrations, generating correlation coefficients for the plurality of measured spectral graphs via an AI module, wherein the correlation coefficients correlate emission intensity and the concentrations of the training samples, automatically developing characteristic profiles for a plurality of elements, compounds, and/or mixtures of two or more elements and/or compounds based on the training data via the AI module on the one or more servers, generating plasma from the analyte using at least one reactor, receiving experimental data for the plasma from a testing spectrometer via the one or more servers, and automatically generating a report with indications and concentrations of present identified molecules based on comparison of the experimental data to the characteristic profiles using the AI module.

In yet another embodiment, the present invention is directed to an artificial intelligence (AI)-based system for automatically identifying molecules in an analyte, including one or more cloud servers configured to receive training data from one or more spectrometers or chemical analysis devices, at least one reactor, and an AI module on the one or more cloud servers configured to automatically develop characteristic profiles for a plurality of elements, compounds, and/or mixtures of two or more elements and/or compounds based on the training data wherein the training data corresponds with training samples of known elements, compounds, and/or mixtures of two or more elements and/or compounds, wherein the training data received from the one or more spectrometers or chemical analysis devices is stored on the one or more cloud servers, wherein the at least one reactor is operable to generate plasma from the analyte, wherein the one or more cloud servers receive experimental data for the plasma from a testing spectrometer, wherein the AI module automatically generates a report with indications of present identified molecules based on comparison of the experimental data to the characteristic profiles, wherein the AI module automatically generates updated characteristic profiles based on a combination of the stored training data and new training data when the new training data is received from the one or more spectrometers or chemical analysis devices, and wherein the AI module automatically generates an updated report with indications of identified molecules based on comparison of the experimental data to the updated characteristic profiles.

Spectroscopic techniques are a quintessential method of analyzing chemical composition of analytes. Various spectroscopic techniques rely on different techniques to treat an analyte and rely on different phenomena of molecules in order to identify the analyte. For example, infrared (IR) spectroscopy involves emitting infrared radiation on an analyte and then detecting the absorbance of the radiation from the molecules within at different wavelengths. The vibrational modes of particular functional groups or bond types within the material tend to absorb infrared radiation at different wavelengths, allowing for determination of at least properties of one or more chemical components within the analyte. Most commonly, spectroscopic tests are performed for analytes with one or only a few unknown components, allowing for simpler, albeit not always very simple, investigation of the composition of a small number of chemicals. However, difficulty arises in these techniques where there are many components having different functional groups, especially where those different components are larger and have more functional components.

Difficulties arise, in part, because analytes with many types of molecules tend to produce a high density of peaks within the technique that are difficult for a human operator to accurately distinguish or determine whether higher peaks indicate multiple components with the same functional group or a single component having the group, but having high concentration. For complex analytes such as organic compounds and medical fluids, these issues have partially been resolved by utilizing a wide array of tests for the same sample types, where the variety of tests are able to detect the presence or absence of specific molecules or classes of molecules. For example, for blood analysis, a wide variety of tests, from enzymatic tests and flow cytometry, to Raman spectroscopy and beyond are used to provide a more comprehensive view of the blood sample. However, the use of this wide variety of test techniques also necessitates higher expense and longer time than is ideal for informing patients about potentially serious issues that require resolution. Most commonly, not all of these tests are capable of being performed in the doctor's office or hospital, extending the time even further to account for transport of samples and communication with an external lab. Therefore, a method is needed to simplify analysis of sample analytes to utilize a single device (or a relatively low number of devices) in order to reduce time and money required for analysis.

Optical emission spectroscopy (OES), specifically, is a widely used analytical technique to determine the chemical composition of a variety of elements and compounds, typically for determining the elemental composition of metals. In optical emission spectroscopy, spectral lines are emitted by every analyte (element or compound) and are unique to that analyte. The emission lines from the analyte then enter the spectrometer and become split into spectral wavelengths by a diffraction grating element in the spectrometer. The intensity of light for each spectral wavelength is then detected by a corresponding detector. A computer system then measures the intensity of the spectral lines in the spectrum to determine the concentration of each element in the analyte.

However, OES as a technique begins to struggle when it analyzes samples with many kinds of molecules. These samples tend to produce a high density of spectral emission wavelengths which make it difficult for a human operator to accurately distinguish whether higher intensities indicate multiple components with the same functional group or a single component at a higher concentration. Higher resolution optical emission spectrometers can overcome this problem by improving the spectral resolution. However, these optical spectrometers are more expensive and require extensive data collected over long periods of time to produce accurate results.

Pixel resolution and spectral resolution are two key parameters which determine spectrometer performance. Pixel resolution determines how the spectrum is quantized after light is measured by the spectrometer. A smaller pixel resolution means that the spectrum is quantized into a fewer number of "bins" or pixels and thus leads to less detail in the data from the spectrometer.

Due to non-idealities in the optics of a spectrometer, some shifts in wavelength may occur when using a spectrometer. While pixels of a spectrometer detector associated with the actual emission wavelengths will receive the greatest light intensity, pixels nearby the actual emission wavelengths will receive a lesser light intensity according to a falloff curve.

Spectral resolution is then defined as the width of the collection of pixels which receive a light intensity above half of the peak light intensity. Spectral resolution is dependent on the pixel resolution but also depends on the optics of the spectrometer; for example, a larger slit in the spectrometer can lead to greater dispersion in the wavelength of light that reaches the light detector, and therefore a lesser spectral resolution. Increasing pixel resolution and spectral resolution typically requires expensive and specialized hardware that can be difficult to obtain. Therefore, a system is needed to accurately distinguish wavelengths from an analyte on a spectrum in a cost-effective manner with a lower pixel and spectral resolution.

Additionally, prior art spectroscopy methods typically rely on one or a few characteristic wavelengths or peaks for detection of the composition of an analyte. This approach does not account for other indicators of the presence of an analyte, such as a faint baseline rise or a dip at an unusual wavelength that correlates with analyte levels. By analyzing not just a single spectral line on a particular wavelength and analyzing patterns for detection of analytes at multiple wavelengths, the present invention provides for detection of analytes that traditional spectroscopy methods do not detect.

Therefore, a method is needed to improve the analysis of analytes from low-cost optical emission spectroscopy, in order to reduce the time and money required for analysis and provide accurate detection of analytes with unknown compositions which include many elements and/or compounds that traditional spectroscopy fails to detect.

Referring now to the drawings in general, the illustrations are for the purpose of describing one or more preferred embodiments of the invention and are not intended to limit the invention thereto.

The present invention is operable to analyze the full spectrum graph of an analyte, which comprises an element, a compound, and/or any combination of any number of elements and/or compounds. The collection of elements and/or compounds which are analyzed are able to be highly complex, for example the present invention is operable to analyze the full spectrum graph of an organic sample analyte. Prior art spectroscopy methods typically rely on a single (or a few) spectral line(s) on a particular wavelength (s) to detect elements and/or compounds in an analyte. The present invention advantageously allows for a holistic analysis because looking at the entire spectrum allows for detection of patterns that traditional spectroscopy methods do not detect.

The present invention includes a device (e.g., a computer, a smart phone, a tablet, a smart watch, etc.) including a processor and a memory operable to receive and analyze spectrographic test data from at least one spectrographic analysis device, especially an optical emission spectroscopy (OES) spectrometer. In one embodiment, the device includes at least one server in network communication directly with the at least one spectrographic analysis device, or through an intermediary device, such as a computer, tablet, smart phone, etc. In this embodiment, analysis is able to be done remotely, providing for additional computational power and sharing of spectroscopic data and test results. In one embodiment, the at least one server includes at least one quantum processor operable to assist in performing analysis on the spectrographic test data.

The present invention is operable to produce a multi-dimensional dataset of spectral data or other chemical analysis data generated by one or more spectrometers or other chemical analysis devices. This multi-dimensional data allows the AI model of the present invention to leverage diverse and orthogonal information from each dimension in the dataset to allow for a final classification of molecules or compounds in an analyte. In one embodiment, the dataset is multimodal, meaning that the system of the present invention is capable of combining different analysis modalities (e.g., UV spectra, Raman spectra, IR spectra, mass spec, etc.) whether produced by a single device or multiple different devices. This combination of multiple modalities allows the system to become more granular and precise in its evaluations. In addition to different spectral or other analysis data, the multi-dimensional dataset is further able to take into account additional modalities, including patient demographics (e.g., race, sex, age, etc.), patient medical history, patient vitals, location where a sample was taken, and/or other parameters, which often assist in providing additional context to measurements in a medical environment. In one embodiment, patient demographic data or other similar data is connected to the chemical analysis (e.g., spectroscopic data) as metadata in order to allow for association of the patient demographics with the particular samples. The multi-dimensional dataset is able to be generated at the chemical analysis devices or at the server itself as it combines data from different data sources.

The present invention is preferably able to be used for analysis of medical fluids (i.e., fluids generated by a human body or the body of another, non-human animal). Furthermore, the term "fluid" as used herein is used to refer to both gasses and liquids. Examples of medical fluids able to be analyzed by the present invention include blood, saliva, urine, sweat, lymph, amniotic fluid, synovial fluid, mucus, semen, and/or other medical fluids. However, the present invention is advantageously operable to analyze other analytes, such as organic fluids, organic compounds, environmental samples such as water or soil, and heavy metals and alloys. One skilled in the art will realize that optical emission spectroscopy (OES) is advantageous for other families of elements and molecules, and will further realize that the analysis of the present invention can be applied to various other methods of spectroscopy, each of which having their different advantages. Therefore, the above list is shortened for brevity and clarity.

In one embodiment, the analytes are analyzed directly using a spectrometer. In another embodiment, the analytes are mixed or dissolved with a solvent, including by way of example and not limitation, water, nitric acid, formic acid, dichloromethane, hexane, methanol, acetonitrile, other volatile organic solvents, and any combination thereof. In a further embodiment, before analyzing an unknown analyte, the solvent to be used is itself analyzed to establish a baseline. Any spectrographic test data then collected is normalized against the established baseline of the solvent to create data only showing the emission spectra of the solute. By mixing the analyte with a solvent before analyzing it with a spectrometer, organic compounds are more easily analyzed by the spectrometer without unintentionally denaturing, transforming, or otherwise marring the compounds.

The present invention is preferably used with optical emission spectroscopy (OES). Using OES, the present invention generates plasma of the analyte to be analyzed and analyzes the light emitted from the plasma. In a further embodiment, an optical cable (e.g. a fiber optic cable) is attached to a chamber where the plasma is generated to transmit the light to the optical emission spectrometer. In one embodiment, the plasma generated by the system is non-thermal plasma. In one embodiment, the chamber where the plasma is generated is subject to a vacuum to achieve zero air pressure or near-zero air pressure. The system of generating plasma, specifically non-thermal plasma, is described in further detail in U.S. patent application Ser. No. 18/805,927, which is incorporated herein by reference in its entirety.

However, the present invention is not necessarily limited to OES spectroscopy. Examples of spectroscopic techniques whose results are able to be examined according to the present invention include ultraviolet-visual (UV/Vis) spectroscopy, near infrared (NIR) spectroscopy, infrared (IR) spectroscopy, Raman spectroscopy, mass spectrometry, nuclear magnetic resonance (NMR) spectroscopy (including continuous wave, Fourier-Transform, solid state NMR, magic-angle spinning NMR, etc.), X-ray spectroscopy, atomic emission spectroscopy (AES), Mossbauer spectroscopy, and/or other forms of spectroscopic and spectrophotometric techniques. Likewise, while the present invention recites "emission intensity" when describing the output of a spectrometer, different methods of spectroscopy measure different variables with respect to wavelength, such as absorption of light. As such, emission intensity should be understood in the present invention to refer to the output of the type of spectrometry used.

FIG. 1 illustrates an exemplary system of the present invention. The present invention comprises a chamber 100 configured to generate non-thermal plasma from the analyte and furthermore captures light from the plasma for analysis. The chamber is connected via optical cable to a spectrometer 110, which measures the light from the non-thermal plasma and generates spectrographic test data based on the light. The spectrographic test data is then sent to processor 120, which performs the aforementioned analysis on the spectrographic test data.

The processor of the device includes an artificial intelligence (AI) engine, comprising at least one artificial intelligence model. The AI engine and its model are operable to perform analysis on the spectrographic test data and identify at least one element or compound within the unknown analyte. The artificial intelligence engine and the model are further operable to determine the concentration of the at least one element or compound within the unknown analyte. In one embodiment, the artificial intelligence engine is operable to output likelihoods associated with the at least one element or compound within the unknown analyte, based, at least in part, on closeness of match to previous data or a model built based on analysis of previous data. The artificial intelligence engine and its model are described in further detail in U.S. Patent Publication No. 2025/0111900, which is incorporated herein by reference in its entirety.

The artificial intelligence model is particularly advantageous due to the holistic full-spectrum nature of its analysis. Traditional spectroscopic analysis takes into consideration only a few notable emission peaks of elements or compounds during identification. If these notable emission peaks are not identifiable, for example due to two compounds overlapping in emission at a specific wavelength, traditional spectroscopy typically mischaracterizes or fails to identify all the components of an unknown analyte. The artificial intelligence model of the present invention, however, is operable to identify and perform pattern matching on all features of emission spectra of elements or compounds. Therefore, even if the most notable emission peak of an element or compound overlaps with another component of the unknown analyte, the artificial intelligence model is operable to perform pattern matching on less notable features of the element or compound to correctly identify it in the unknown analyte. These less notable features are often ignored or unnoticed in traditional spectroscopy. In this way, identification of all components of an analyte is improved over traditional spectroscopy, even in a complex sample with a crowded and overlapping emission spectrum.

Even if the emission spectra of two compounds do not exactly overlap, exact determination of their peak wavelengths (and thus determining the presence of the compounds) can prove difficult with conventional spectroscopy. If a spectrometer with lower wavelength resolution is used, there may not be enough clarity in the spectrographic test data to tell these peaks apart. This renders analysis of complex analytes using conventional spectroscopy impossible without prohibitively expensive high-resolution spectrometers, increasing the cost of sample analysis. Using the artificial intelligence model of the present invention, a spectrometer resolution high enough to discern two partially overlapping prominent emission peaks is not required; the artificial intelligence model is operable to perform pattern matching on less prominent features of the spectrographic test data, eliminating the need to discern the two partially overlapping peaks in the first place.

In one embodiment, the at least one artificial intelligence module is trained based on a plurality of prepared training data. Preferably, this training data corresponds with analytes with known chemical compositions, such that the at least one artificial intelligence module is able to correlate the output spectrographic test data with the known chemical composition to build a more accurate model. In this way, the system develops a characteristic profile for each molecule, or set of molecules such that, under similar conditions and showing similar spectra, the system is able to identify particular molecules with a particular degree of certainty. The training data comprises spectral graphs, preferably multiple spectral graphs for each element or compound. For the training data, each element or compound is measured alone, or mixed or dissolved into a known solute as described above. In one embodiment, training of the artificial intelligence model employs early stopping based on validation loss and/or network regularization with dropout layers and/or L2 weight penalties.

For each element or compound, different measurements may vary testing parameters, for example the integration time of the analysis, the pressure of the chamber where plasma of the analyte is generated, the wavelength or intensity of the exciter which excites the analyte into plasma, the slit width of the spectrometer, and/or the spectral resolution of the spectrometer. One skilled in the art will realize that many different parameters may be varied to produce more comprehensive results and training data, and the number of recited parameters has been limited for clarity and brevity. In a preferred embodiment, and especially when identifying the concentration of the elements or compounds, the training data includes multiple measurements and spectral graphs for each element or compound, wherein the concentration of the element or compound is varied.

An example of such training data, which measures the emission lines of various elements, is the NIST Handbook of Basic Atomic Spectroscopic Data, version 1.1.3, dated November 2013. However, it is important to note that the present invention measures all elements and compounds by generating plasma of the analyte, rather than the varying spectroscopy methods of the NIST data. Furthermore, training data for the purposes of the present invention should include multiple measurements for each element and compound where the concentration of the element or compound is varied.

In one embodiment, the training data further includes synthetic data (i.e., data not from actual tests) in order to expedite the model learning simple spectra of common molecules. The use of an artificial intelligence module is especially important for analytes which comprise complex molecules that are unlikely to show simple peaks that are easily understood or reasoned out by a researcher (due to factors such as density of peaks and greater noise).

In one embodiment, the training data further includes measured emission lines of mixtures comprised of two or more elements and/or compounds. The AI module is operable to be trained on the emission spectra of the mixtures and the known concentrations of the elements and/or compounds which comprise the mixture. In one embodiment, the AI module is operable to analyze an unknown compound and identify at least one mixture comprising the unknown compound. By training the AI model on more complex substances, the AI model can learn how the emission lines of elements and/or compounds comprising the mixture interact with one another, to more accurately and efficiently provide the chemical composition of an unknown substance.

In one embodiment, the training data is operable to be preprocessed. Each raw spectrum is calibrated against known reference lines from, for example, a calibration lamp, and then is operable to be normalized by total emission or an internally defined reference line. In a further embodiment, the training data is further processed to identify the most relevant portions of spectrum. The processor is first operable to divide the spectrum graphs of the training data into at least one wavelength bin. For each wavelength bin, a correlation coefficient is then calculated. In an alternative embodiment, a correlation coefficient is calculated for each wavelength of the spectrum graphs.

The correlation coefficient describes how strongly the emission intensity correlates to the concentration of an element or compound. This correlation coefficient is a numerical value which varies from −1 to 1, where −1 represents a strong negative correlation, 1 represents a strong positive correlation, and 0 represents no correlation. Therefore, if the correlation coefficient is 1, an increase in concentration of the analyte leads to a higher emission intensity. Likewise, if the correlation coefficient is −1, an increase in concentration of the analyte leads to a lower emission intensity. This negative correlation might occur if the analyte absorbs certain wavelengths of light, especially if it is dissolved in a solvent and absorbs some of the emissions of the solvent. One skilled in the art will realize there may be more reasons for observing negative correlations, especially considering non-thermal plasma generation is an emerging innovation. In one embodiment, the correlation coefficients are used to determine a confidence interval for the training data.

In one embodiment, the AI model is operable to be trained on the training data and learn patterns in emission spectrum from the training data. In one embodiment, the AI model is of any type operable to learn features using a plurality of weights. The AI model is operable to learn the training data such that accuracy in determining chemical composition improves over time. The trained AI model allows quick identification of chemical composition at high levels of accuracy.

In one embodiment, the correlation coefficient is operable to be used to select the wavelength bins of the spectrum graphs of the training data which are used to train the artificial intelligence model. For example, if the absolute value of the correlation coefficient is above a certain value (e.g. p=0.4), the emission intensities for that bin are given to the artificial intelligence model for training, and other bins are discarded to reduce noise in the AI system.

Figure 2B:
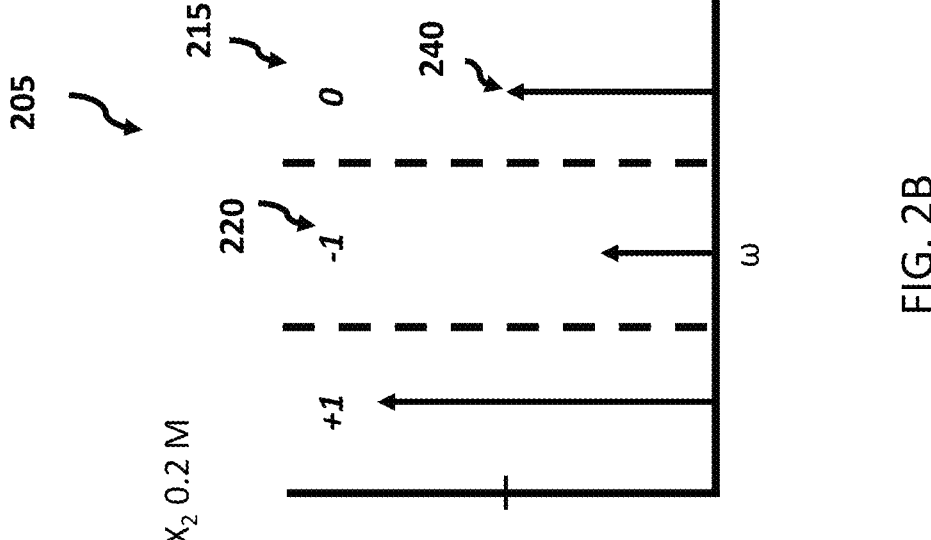
FIG. 2B illustrates a subdivided spectral graph of the present invention.
Figure 2A:
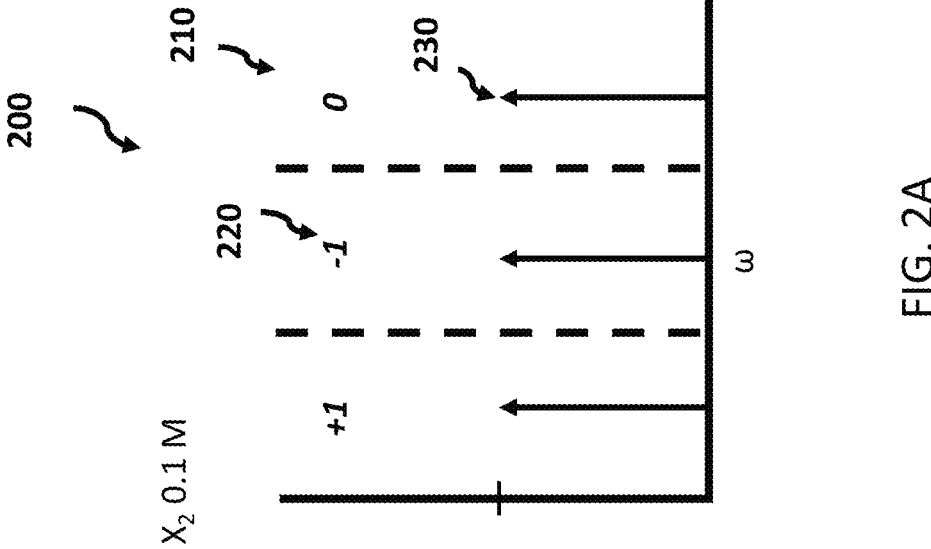
FIG. 2A illustrates a subdivided spectral graph of the present invention.

FIG. 2A and FIG. 2B illustrate the correlation coefficients for a hypothetical compound $X_2$. Two emission spectrum graphs 200, 205 are shown for different concentrations of the compound, at 0.1 moles on the left and 0.2 moles on the right. Three bins 210, 215 are created for each emission spectrum graph. The correlation coefficients 220 are shown for each bin. At 0.1 moles, the compound has equal emission intensities 230 at three points along the spectrum graph 200, however each emission intensity is contained within bins with different correlation coefficients (from left to right, +1, −1, and 0). As the concentration of the compound increases, as shown in spectrum graph 205, the expected emission intensities 240 change based on the correlation coefficients of their bins 215. For the +1 bin, the emission intensity increases when concentration increases; for the −1 bin, emission intensity decreases when concentration increases; and for the 0 bin, there is no change in emission intensity with respect to concentration.

In one embodiment, the artificial intelligence engine is operable to generate correlation functions between the emission intensity and the concentration of an element or compound. The artificial intelligence engine develops a line of best fit which follows a log-linear fit, a first degree, second degree, or n-degree polynomial fit, a linear fit, an exponential fit, or any other best-fit line. In a further embodiment, a separate line of best fit is developed for each of the wavelength bins of the spectrum graph, corresponding with the correlation coefficients of each bin.

In one embodiment, the trained AI model is operable to receive an emission spectrum from an unknown analyte. The trained AI model is operable to identify and perform pattern matching on all features of the emission spectrum to determine the chemical composition of the unknown analyte. Furthermore, the trained AI model is operable to dynamically adjust spectrometer parameter settings including integration time, spectral resolution and/or entrance slit width to reduce noise and/or saturation in the emission spectrum.

The trained AI model is advantageous at determining the composition of an unknown analyte. When testing a trained AI model, there are three relevant performance indicators: accuracy, precision, and recall. Accuracy is the ratio of correct predictions to all predictions made, precision is the ratio of correct positive identifications to all positives identified by the trained AI model, and recall is the ratio of correct positive identifications to all positive cases in the testing dataset. The accuracy, precision, and recall of an exemplary trained AI model according to the present invention, compared to the typical accuracy, precision, and recall of an inductively coupled plasma mass spectrometry (ICP-MS) system, is listed in Table 1 below:

| Analyte | Accuracy (%) | Precision (%) | Recall (%) | Type | ICP-MS Accuracy (%) | ICP-MS Precision (%) | ICP-MS Recall (%) |
|---|---|---|---|---|---|---|---|
| Acetonitrile | 95.38 | 98.1 | 77.11 | VOC | 95 | 95 | 85 |
| Butanol | 96.04 | 72.32 | 88.04 | VOC | 95 | 88 | 85 |

-continued

| Analyte | Accuracy (%) | Precision (%) | Recall (%) | Type | ICP-MS Accuracy (%) | ICP-MS Precision (%) | ICP-MS Recall (%) |
|---|---|---|---|---|---|---|---|
| Ethanol | 95.66 | 91.82 | 81.56 | VOC | 95 | 90 | 85 |
| Formaldehyde | 99.15 | 100 | 78.57 | VOC | 96 | 96 | 85 |
| Formic Acid | 97.83 | 91.84 | 70.31 | VOC | 94 | 90 | 80 |
| Methanol | 97.26 | 97.37 | 81.02 | VOC | 96 | 92 | 85 |
| Propanol | 99.15 | 76.67 | 92.00 | VOC | 95 | 90 | 90 |
| Tetrahydrofuran | 97.26 | 94.34 | 65.79 | VOC | 94 | 88 | 80 |
| Molybdenum | 99.40 | 100 | 92.60 | Heavy Metal | 96 | 94 | 85 |
| Chromium | 99.99 | 100 | 98.80 | Heavy Metal | 97 | 94 | 90 |
| Mercury | 99.67 | 99.94 | 98.80 | Heavy Metal | 97 | 94 | 88 |
| Fluoride | 99.99 | 100 | 98.90 | Non-metal | 95 | 90 | 80 |
| Titanium | 99.77 | 99.90 | 98.77 | Heavy Metal | 94 | 90 | 80 |
| Selenium | 99.50 | 99.76 | 97.70 | Heavy Metal | 95 | 92 | 85 |
| Antimony | 99.20 | 100 | 95.50 | Heavy Metal | 96 | 92 | 90 |
| Lead | 99.90 | 100 | 98.78 | Heavy Metal | 97 | 95 | 90 |

In an embodiment, the present invention is operable to determine the concentration of identified elements or compounds in the unknown analyte. The trained artificial intelligence model, which has been trained on the training data of elements and compounds with varying concentrations, is operable to determine the concentration of an identified element or compound based on the spectral graph of the unknown analyte. For example, if an analyte contains 2 ppb of lead and 1 ppb of antimony, then after identifying the presence of lead and antimony as described above, the artificial intelligence model is operable to identify the concentrations of each comprising element from the spectral graph of the unknown analyte.

The trained AI model is adept at determining the concentration of identified elements and/or compounds, especially in light of the feature correlation and correlation coefficients of the training step. The percentage of correct concentration predictions of an analyte containing lead within different margins of error is listed below in Table 2:

| Error (%) | Accuracy (%) |
|---|---|
| 10 | 88.64 |
| 20 | 92.05 |
| 30 | 92.05 |
| 70 | 100 |

In one embodiment, the trained artificial intelligence model is operable to continue training while being used to identify unknown analytes. If an element, compound, and/or condition are detected in an unknown analyte, the spectral graph and the identified relevant patterns and features of that analyte are categorized by the element, compound, and/or condition and added to the training data.

In one embodiment, the spectral graphs of analyzed unknown analytes are stored, either locally, on an external server, or in an external cloud environment. When the trained artificial intelligence model is updated, the present invention is operable to re-analyze the spectral graphs of previously measured unknown analytes to more accurately identify elements and/or compounds, and/or to identify elements and/or compounds that were previously not included in the training data. In this manner, the present invention is operable to not only leverage a continually trained model for new unknown analytes but is also operable to use an updated model for previously analyzed analytes.

In one embodiment, the artificial intelligence engine is operable to capture relevant patterns and features from a plurality of unknown analytes, even if those patterns and features cannot be categorized as a previously known element, compound, and/or condition by the trained artificial intelligence model. Since the trained artificial intelligence model is trained on a sometimes limited set of training data, it is expected that the trained artificial intelligence model will encounter patterns and features which the training data does not include, and thus for which the trained artificial intelligence model cannot identify as a known element, compound and/or condition. The artificial intelligence engine is operable to identify reoccurring patterns and features within previously stored unknown analytes and identify spectral contributions which the trained artificial intelligence model is unable to correlate to a known element, compound, and/or condition.

In one embodiment, identification of unknown spectral contributions is operable to be implemented using a clustering algorithm, such as K-means clustering. The artificial intelligence engine is further operable to generate a report if such a reoccurring pattern and/or feature is found, notifying the user that there is an unknown but often-occurring spectral contribution that could prompt further investigation. In a further embodiment, the artificial intelligence engine is operable to leverage the synthetic data and/or perform a simulation of ionized element and/or compound emissions to predict the one or more elements and/or compounds responsible for an unknown spectral contribution.

In one embodiment, data produced by spectrometers or other chemical analysis devices associated with the present invention are able to be brought into a single cloud environment, optionally also including additional public dataset or other supporting datasets produced by third parties in order to aggregate and strengthen the training data. The cloud environment is further operable to continuously train the trained artificial intelligence model, incorporating new data collected by the spectrometers or other chemical analysis devices associated with the present invention. In this embodiment, the present invention is operable to download updated trained artificial intelligence models from the cloud environment, continually staying up-to-date with a model generated from the aggregated training data.

In this embodiment, all data brought into the cloud environment is anonymized, and in the case of the present invention being used in a medical environment, recording of data is operable to comply with local regulations regarding patient confidentiality. For example, recording of data to the cloud environment is operable to comply with the Health Insurance Portability and Accountability Act (HIPAA) if the present invention is used in the United States. In a further embodiment, the data brought into the cloud environment is geotagged at a non-identifying resolution based on the location at which the data was measured. For example, and not by limitation, geotagging is performed by postal code, by city, or via Internet Protocol (IP) address geolocation. In this manner, regional trends of identification are able to be aggregated as the present invention performs analyses, for example, for the spread of disease or the spread of environmental pollution.

In one embodiment, the report is able to include not only an identification of which molecules are present, but also an indication of the concentration of those molecules and/or a probability value associated with the identification to indicate a degree of certainty to which the model identified the reported molecule.

In one embodiment, the system is operable to produce interactive reports detailing what chemicals or molecules are present in an analyte in different formats depending on the preference of the reader or consumer of the data.

In one embodiment, the at least one artificial intelligence module utilizes principal components analysis (PCA) and/or linear discriminant analysis (LDA) for feature compression in order to feed into the downstream machine learning (ML) model used by the present invention.

The system is operable to utilize a plurality of learning techniques including, but not limited to, machine learning (ML), artificial intelligence (AI), deep learning (DL), neural networks (NNs), artificial neural networks (ANNs), support vector machines (SVMs), transformers (e.g., generative pre-trained transformers), Markov decision process (MDP), random forest, multiple layer perceptron, recurrent neural networks, generalized adversarial networks, and/or natural language processing (NLP). The system is operable to use any of the aforementioned learning techniques alone or in combination.

Further, the system is operable to utilize predictive analytics techniques including, but not limited to, machine learning (ML), artificial intelligence (AI), neural networks (NNs) (e.g., long short term memory (LSTM) neural networks), transformers (e.g., generative pre-trained transformers), deep learning, historical data, and/or data mining to make future predictions and/or models. The system is preferably operable to recommend and/or perform actions based on historical data, external data sources, ML, AI, NNs, and/or other learning techniques. The system is operable to utilize predictive modeling and/or optimization algorithms including, but not limited to, heuristic algorithms, particle swarm optimization, genetic algorithms, technical analysis descriptors, combinatorial algorithms, quantum optimization algorithms, iterative methods, deep learning techniques, and/or feature selection techniques.

FIGS. 3-16 provide examples of spectral data able to be incorporated into the present invention to identify particular molecules and demonstration of the ability of such spectra to distinguish the presence and/or concentration of particular molecules.

Figure 3:
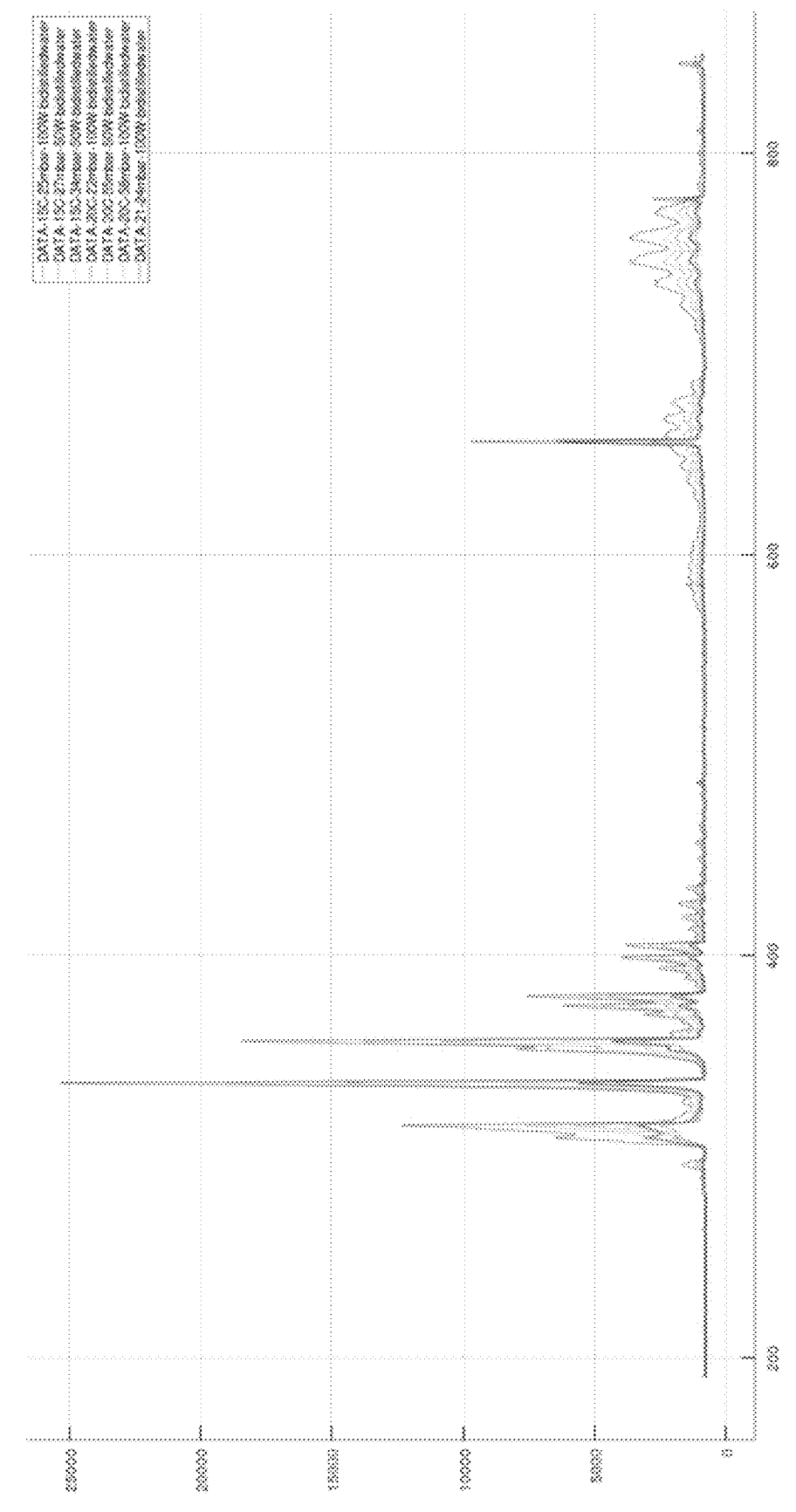
FIG. 3 illustrates a chart of intensity versus wavelength for analysis of bidistilled water at different temperatures and pressures generated by the present invention.
Figure 4:
FIG. 4 illustrates a chart of intensity versus wavelength for analysis of molecular biology grade (MBG) water at different temperatures and pressures generated by the present invention.
Figure 5:
FIG. 5 illustrates a chart of intensity versus wavelength, comparing normalized peaks of bidistilled and molecular biology grade (MBG) generated by the present invention.

FIG. 3 illustrates a chart of intensity versus wavelength for analysis of bidistilled water at different temperatures and pressures generated by the present invention. FIG. 4 illustrates a chart of intensity versus wavelength for analysis of molecular biology grade (MBG) water at different temperatures and pressures generated by the present invention. FIG. 5 illustrates a chart of intensity versus wavelength, comparing normalized peaks of bidistilled and molecular biology grade (MBG) generated by the present invention. As shown in FIGS. 3-5, the device disclosed in the present invention has sufficient sensitivity to detect even different peaks between differently purified or ionized levels of water, demonstrating a high capability for detection of other molecules. For the purposes of analysis, the MBG water spectra was used as a baseline for detecting other molecules as discussed further below.

Figure 6:
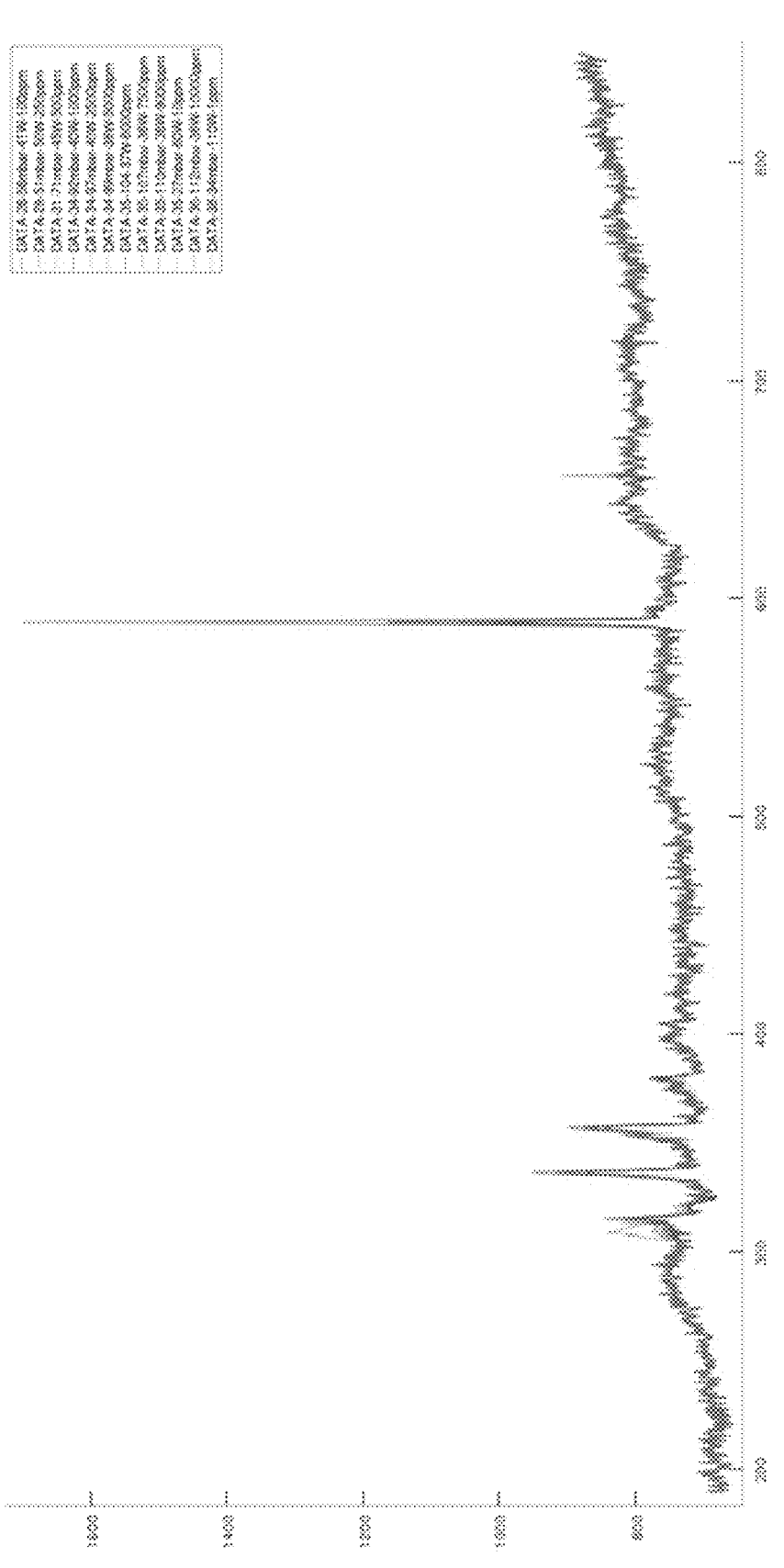
FIG. 6 illustrates a chart of intensity versus wavelength, comparing normalized peaks of sodium chloride (NaCl), dissolved in bidistilled water at different concentrations, pressures, and plasma power conditions generated by the present invention.
Figure 7:
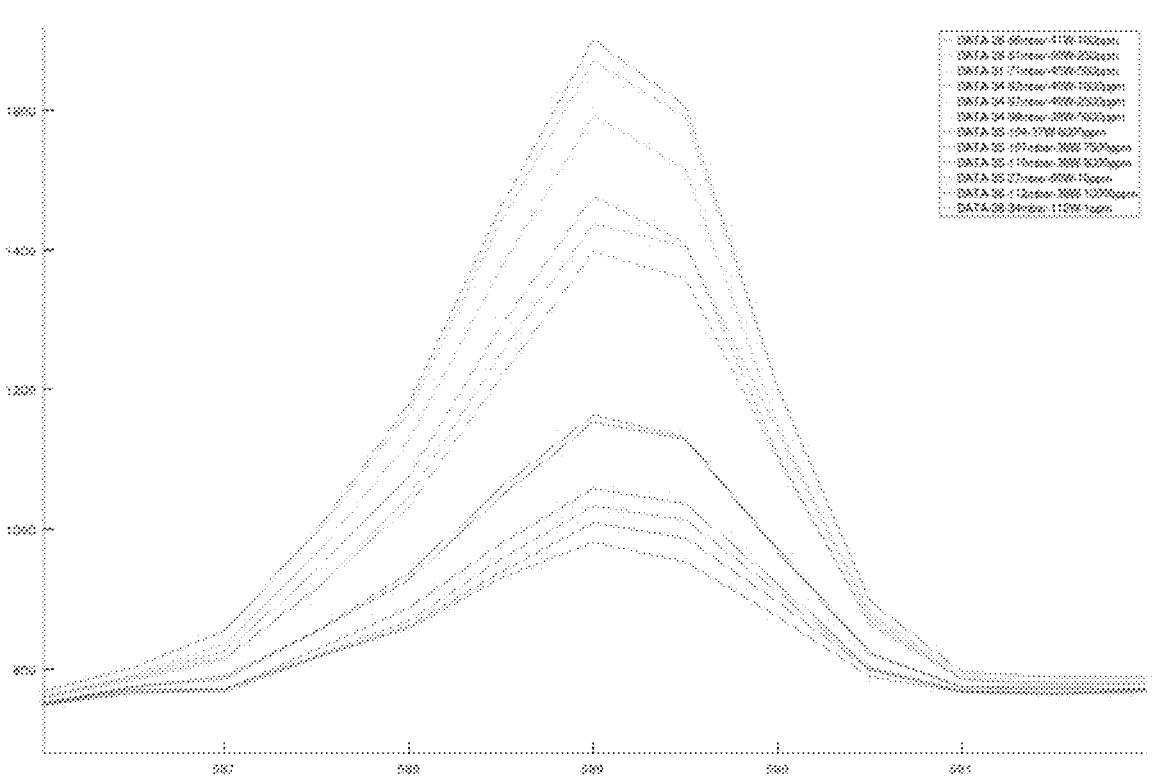
FIG. 7 illustrates a zoomed-in intensity versus wavelength chart for sodium chloride at different pressures, concentrations, and plasma power conditions, focused around a peak at 589 nm generated by the present invention.

FIG. 6 illustrates a chart of intensity versus wavelength, comparing normalized peaks of sodium chloride (NaCl) at different concentrations, pressures, and plasma power conditions generated by the present invention. FIG. 7 illustrates a zoomed-in intensity versus wavelength chart for sodium chloride at different pressures, concentrations, and plasma power conditions, focused around a peak at 589 nm generated by the present invention. By checking the peak at different conditions, including concentrations, pressures, and plasma power conditions, the system demonstrating relatively consistent peaks in the spectrum, but with the peaks having different intensities depending on those conditions. The charts in FIGS. 6-7 demonstrate that, generally, higher peaks are detecting at higher concentrations, allowing the system to have an ability to distinguish amounts of certain chemicals, in addition to identify their presences based on characteristic peaks.

Figure 8:
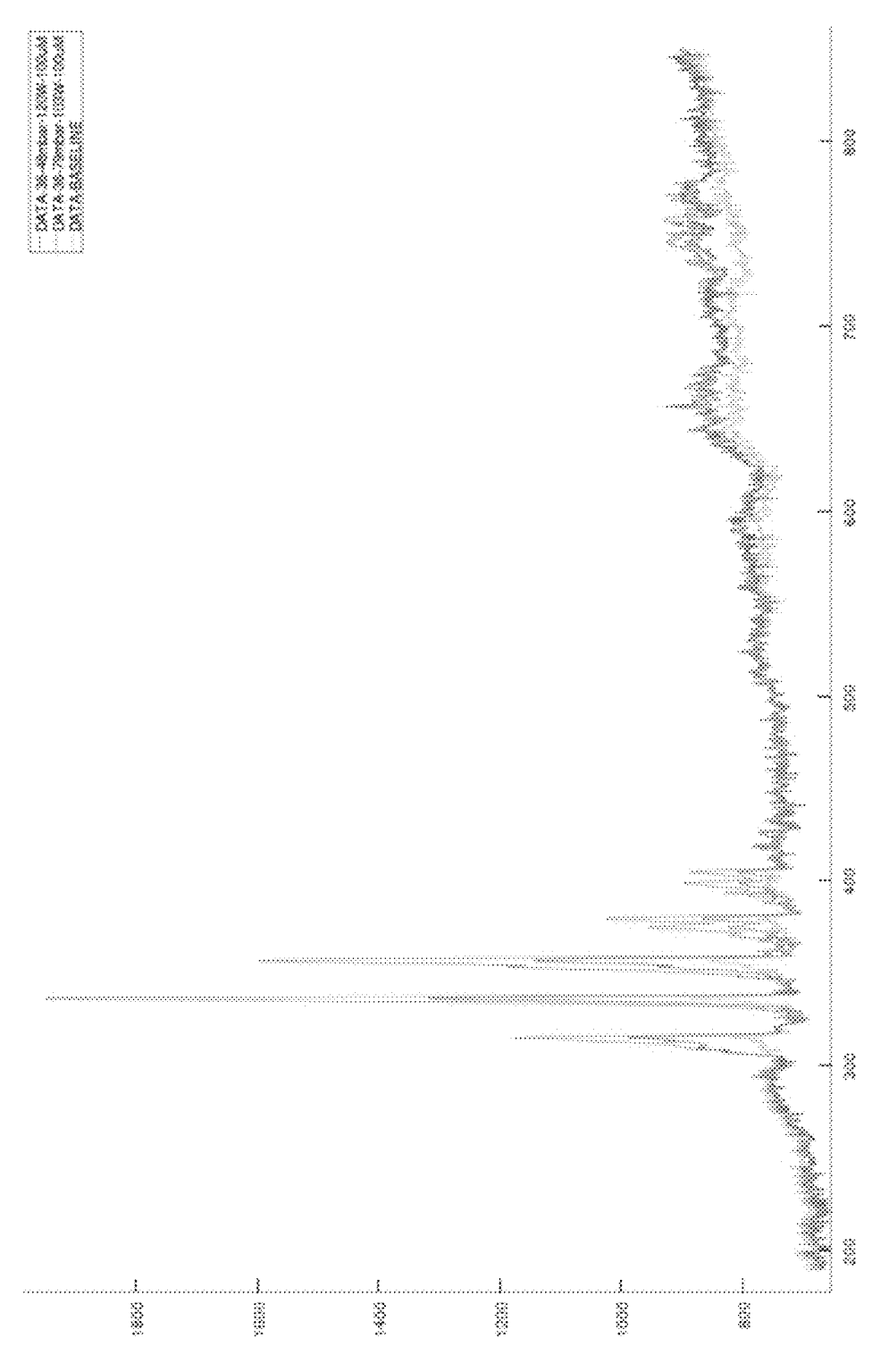
FIG. 8 illustrates a chart of intensity versus wavelength, comparing samples with dATP at different pressure, concentration, and plasma power conditions relative to a water baseline generated by the present invention.
Figure 9:
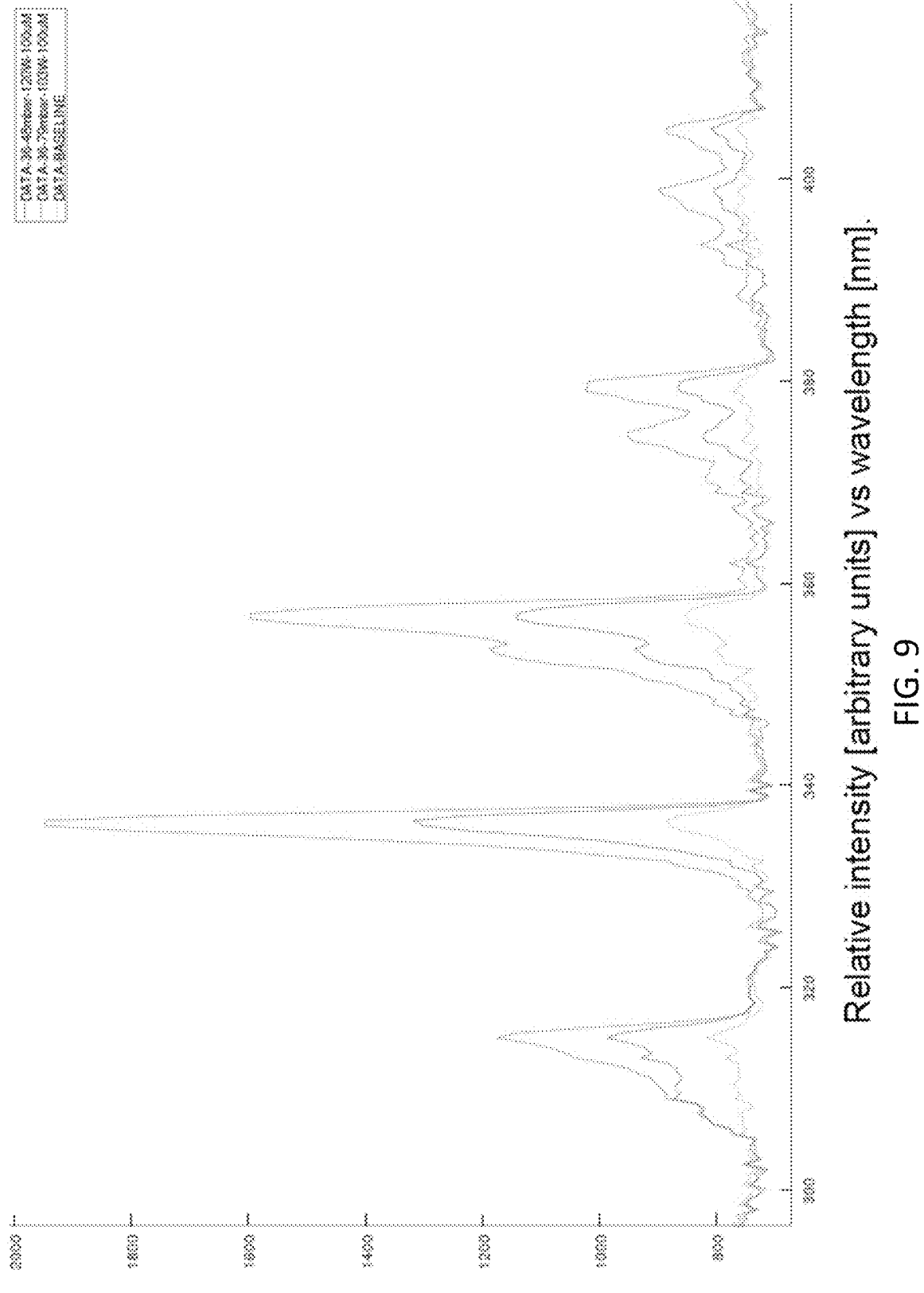
FIG. 9 illustrates a chart of intensity versus wavelength, comparing samples with dATP at different pressure, concentration, and plasma power conditions relative to a water baseline, zoomed in around 360 nm, generated by the present invention.

FIG. 8 illustrates a chart of intensity versus wavelength, comparing samples with dATP at different pressure, concentration, and plasma power conditions relative to a water baseline generated by the present invention. FIG. 9 illustrates a chart of intensity versus wavelength, comparing samples with dATP at different pressure, concentration, and plasma power conditions relative to a water baseline, zoomed in around 360 nm, generated by the present invention. FIGS. 8 and 9 show characteristic peaks that are higher than baseline peaks for the water sample, showing detection of the dATP.

Figure 10:
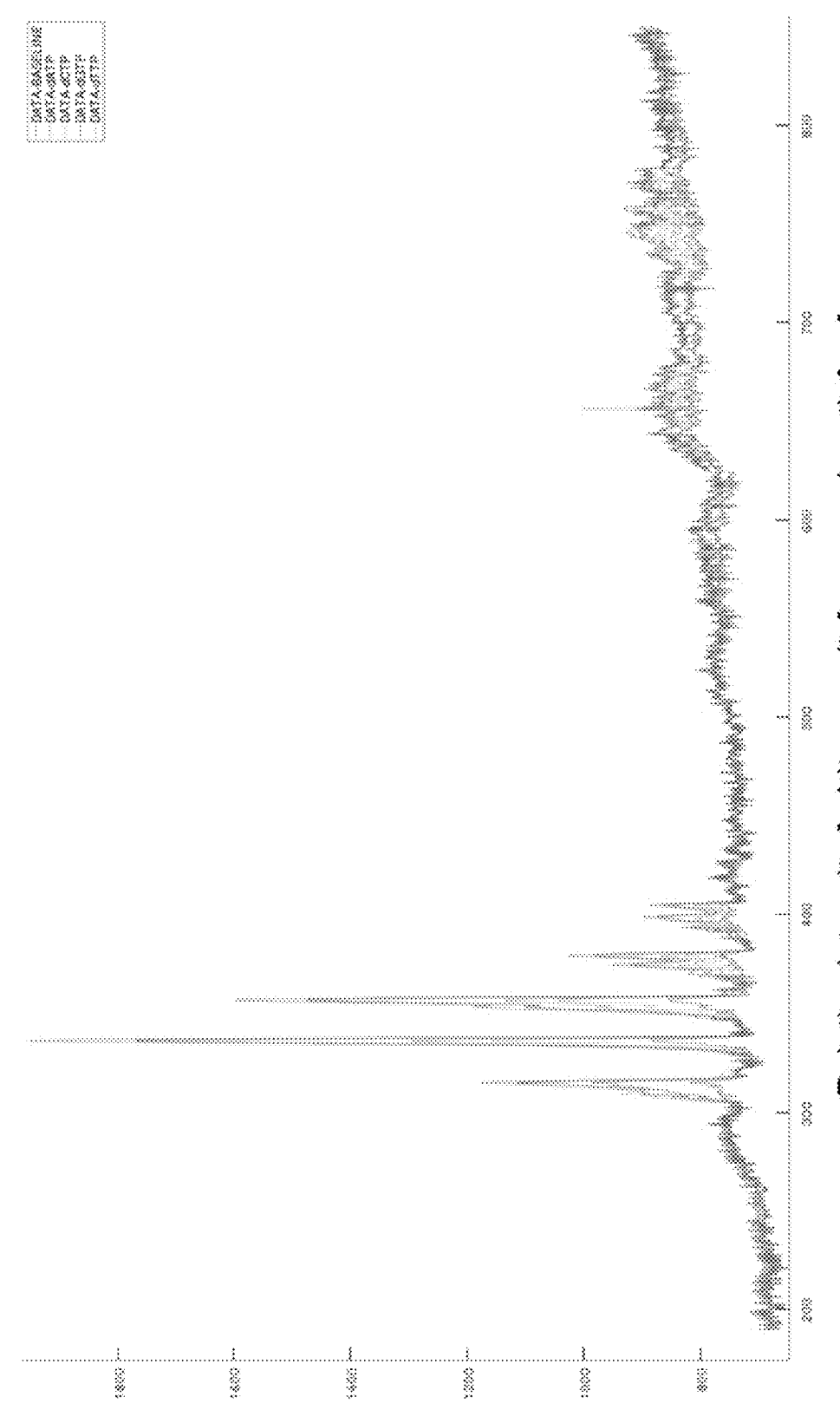
FIG. 10 illustrates a chart of intensity versus wavelength, comparing samples with dATP, dCTP, dGTP, dTTP relative to a water baseline generated by the present invention.
Figure 11:
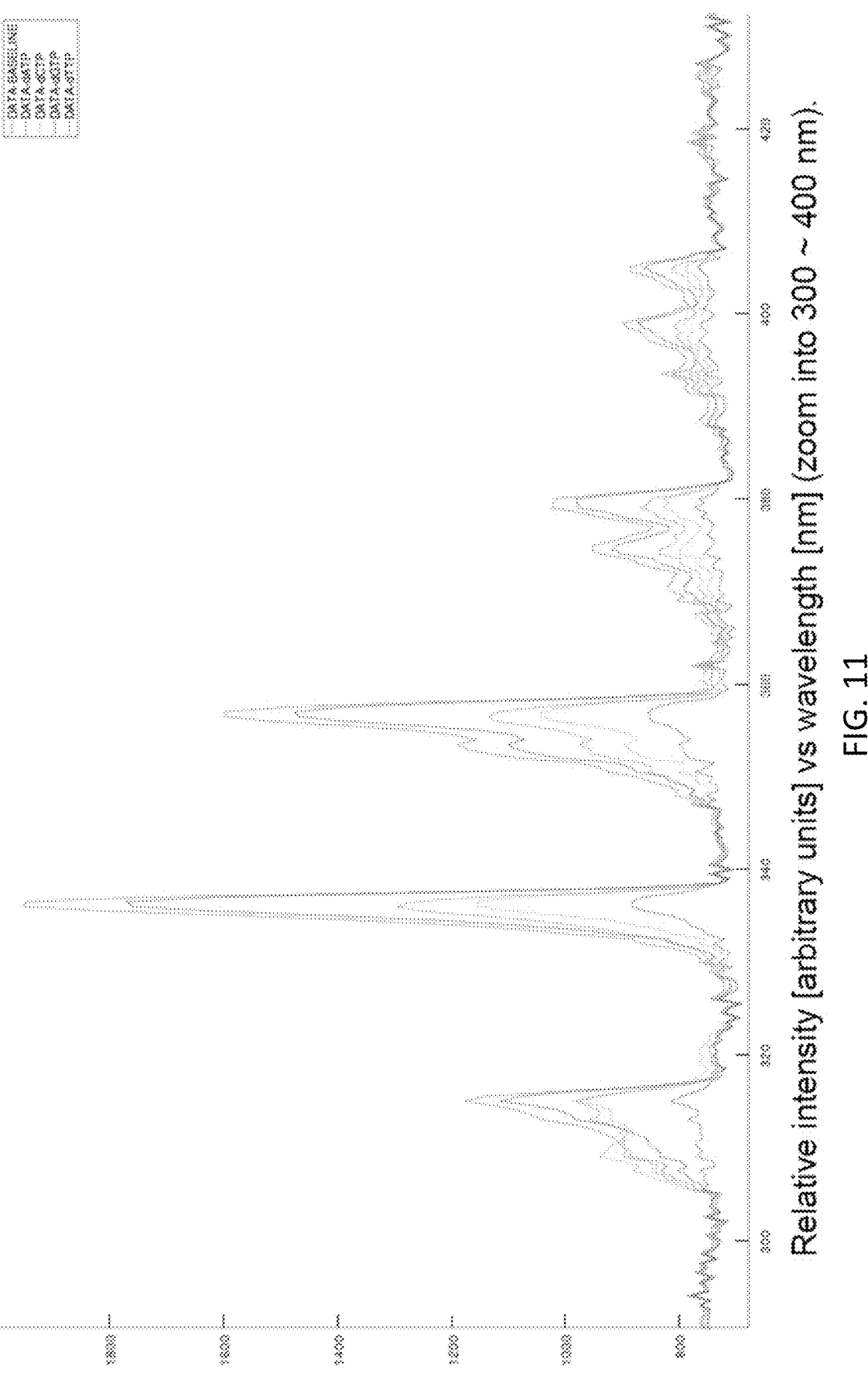
FIG. 11 illustrates a chart of intensity versus wavelength, comparing samples with dATP, dCTP, dGTP, dTTP relative to a water baseline, zoomed in between 300 and 400 nm, generated by the present invention.

FIG. 10 illustrates a chart of intensity versus wavelength, comparing samples with dATP, dCTP, dGTP, dTTP relative to a water baseline generated by the present invention. FIG. 11 illustrates a chart of intensity versus wavelength, comparing samples with dATP, dCTP, dGTP, dTTP relative to a water baseline, zoomed in between 300 and 400 nm, generated by the present invention. FIGS. 10-11 demonstrate that the system is not only capable of detecting a compound present versus a water baseline, but also differentiation between different, but similar, compounds.

Figure 12:
FIG. 12 illustrates a chart of intensity versus wavelength, comparing samples with acetone, ethanol, and MBG water generated by the present invention.
Figure 13:
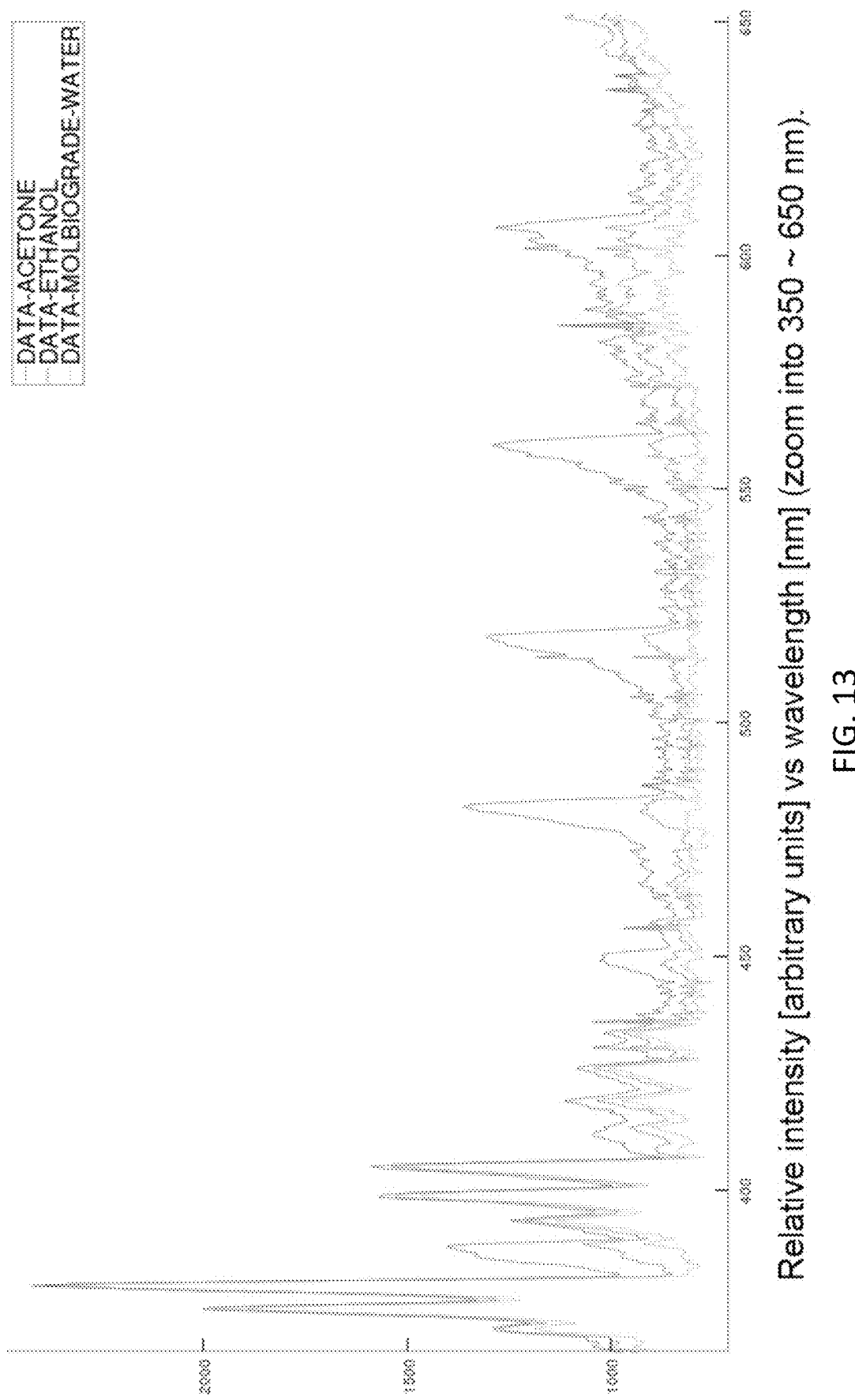
FIG. 13 illustrates a chart of intensity versus wavelength, comparing samples with acetone, ethanol, and MBG water, zoomed in between 350 and 650 nm, generated by the present invention.
Figure 14:
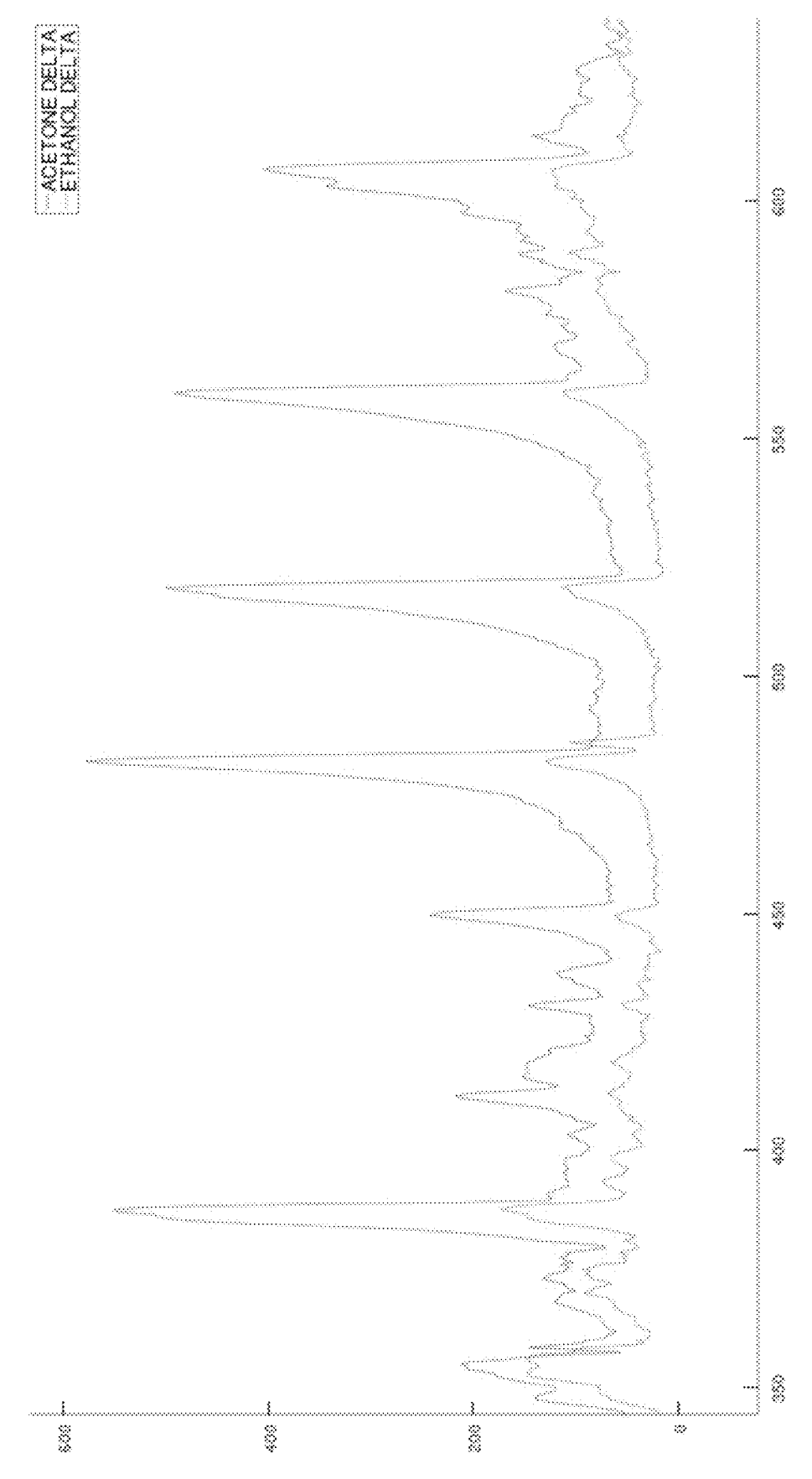
FIG. 14 illustrates a chart of intensity versus wavelength, comparing samples with acetone and ethanol, zoomed in between 350 and 650 nm with the water baseline subtracted, generated by the present invention.
Figure 15:
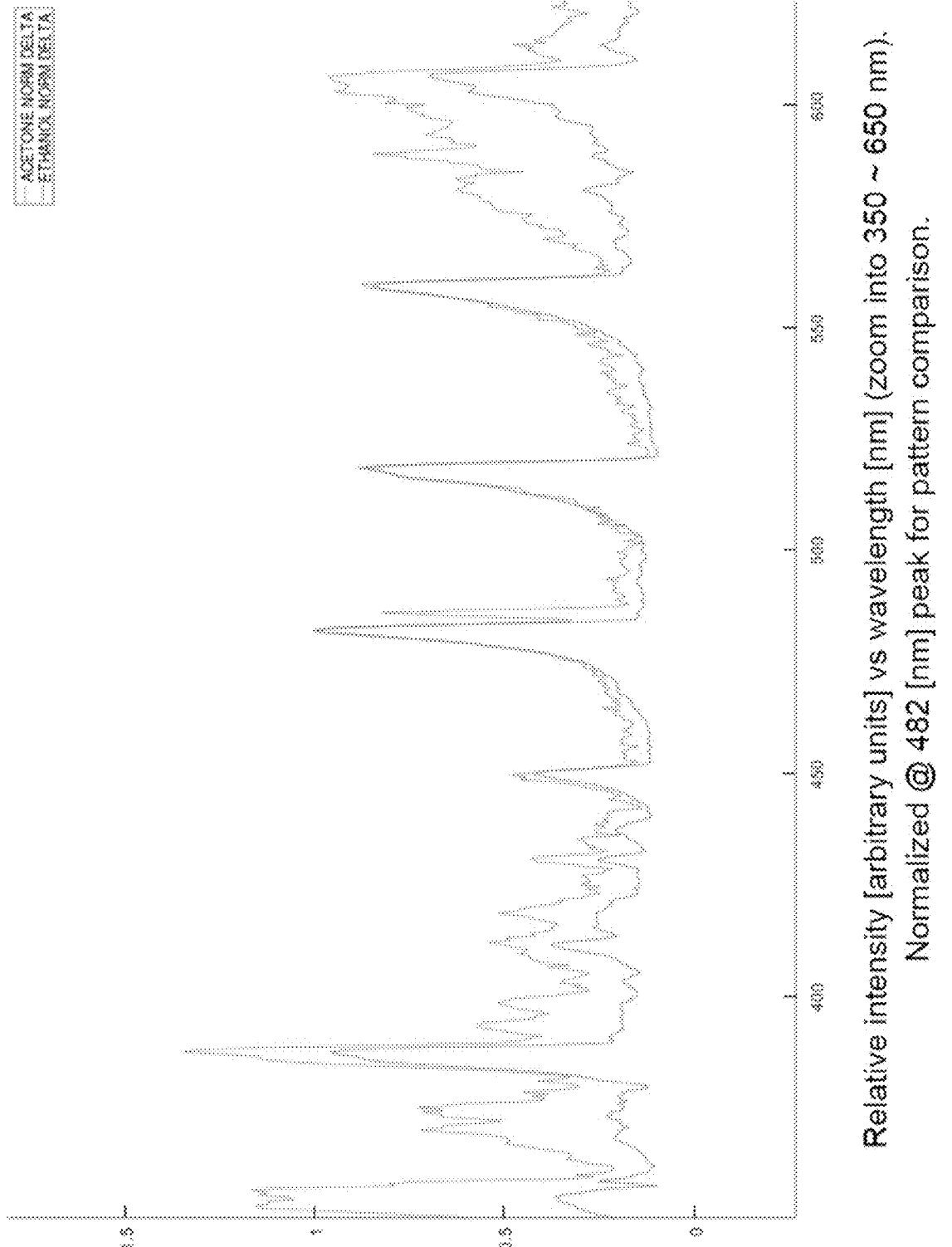
FIG. 15 illustrates a chart of intensity versus wavelength, comparing samples with acetone and ethanol, zoomed in between 350 and 650 nm normalized at a peak at 482 nm, generated by the present invention.
Figure 16:
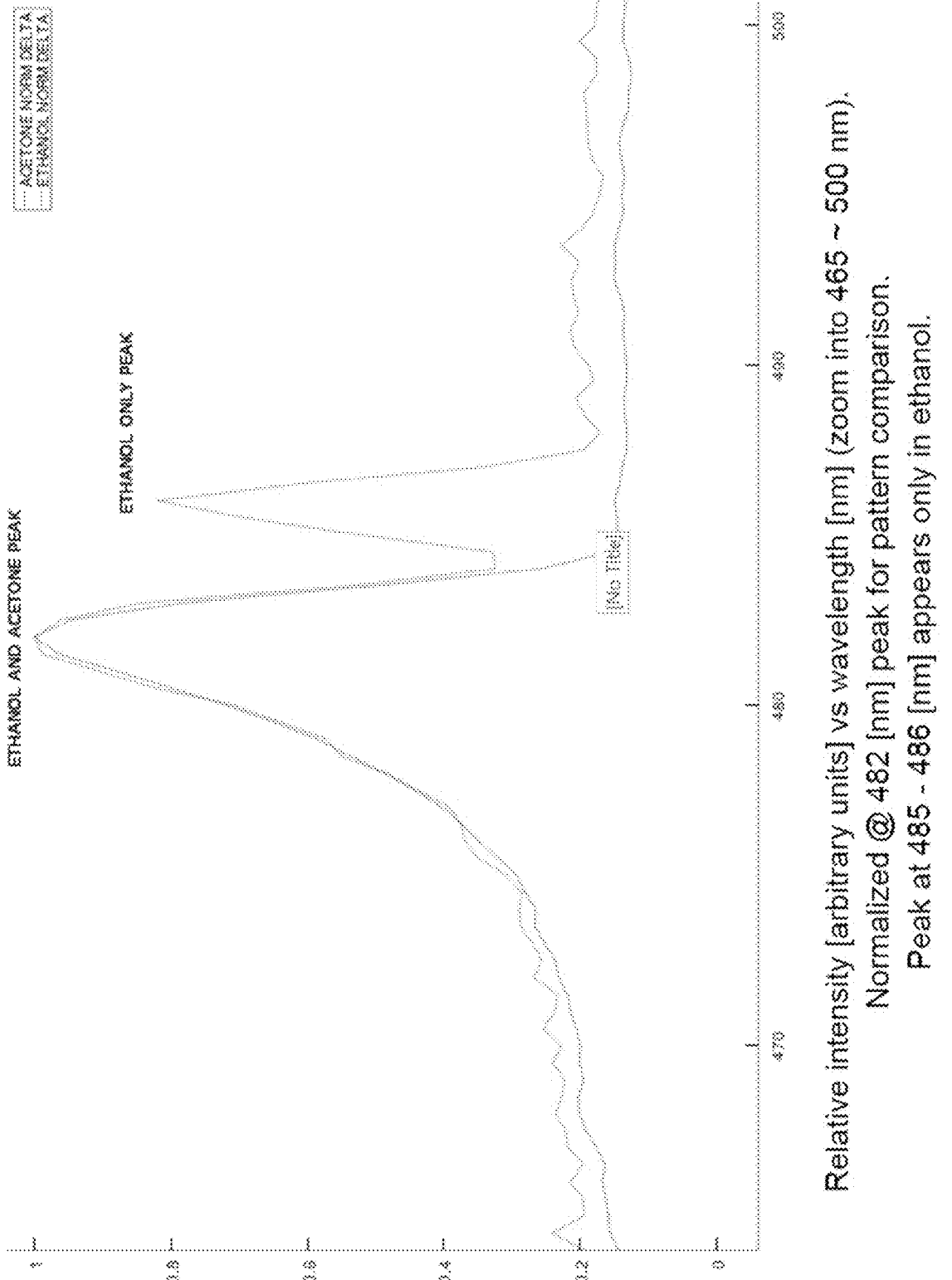
FIG. 16 illustrates a chart of intensity versus wavelength, comparing samples with acetone and ethanol, zoomed in between 465 and 500 nm, showing a peak unique to the ethanol signature at approximately 485 nm, generated by the present invention.

FIG. 12 illustrates a chart of intensity versus wavelength, comparing samples with acetone, ethanol, and MBG water generated by the present invention. FIG. 13 illustrates a chart of intensity versus wavelength, comparing samples with acetone, ethanol, and MBG water, zoomed in between 350 and 650 nm, generated by the present invention. FIG. 14 illustrates a chart of intensity versus wavelength, comparing samples with acetone and ethanol, zoomed in between 350 and 650 nm with the water baseline subtracted, generated by the present invention. FIG. 15 illustrates a chart of intensity versus wavelength, comparing samples with acetone and ethanol, zoomed in between 350 and 650 nm normalized at a peak at 482 nm, generated by the present invention. FIG. 16 illustrates a chart of intensity versus wavelength, comparing samples with acetone and ethanol, zoomed in between 465 and 500 nm, showing a peak unique to the ethanol signature at approximately 485 nm, generated by the present invention. FIGS. 12-16 demonstrate the present invention's ability to differentiate between different simple organic compounds, and particularly between different volatile organic compounds (VOCs).

Figure 17:
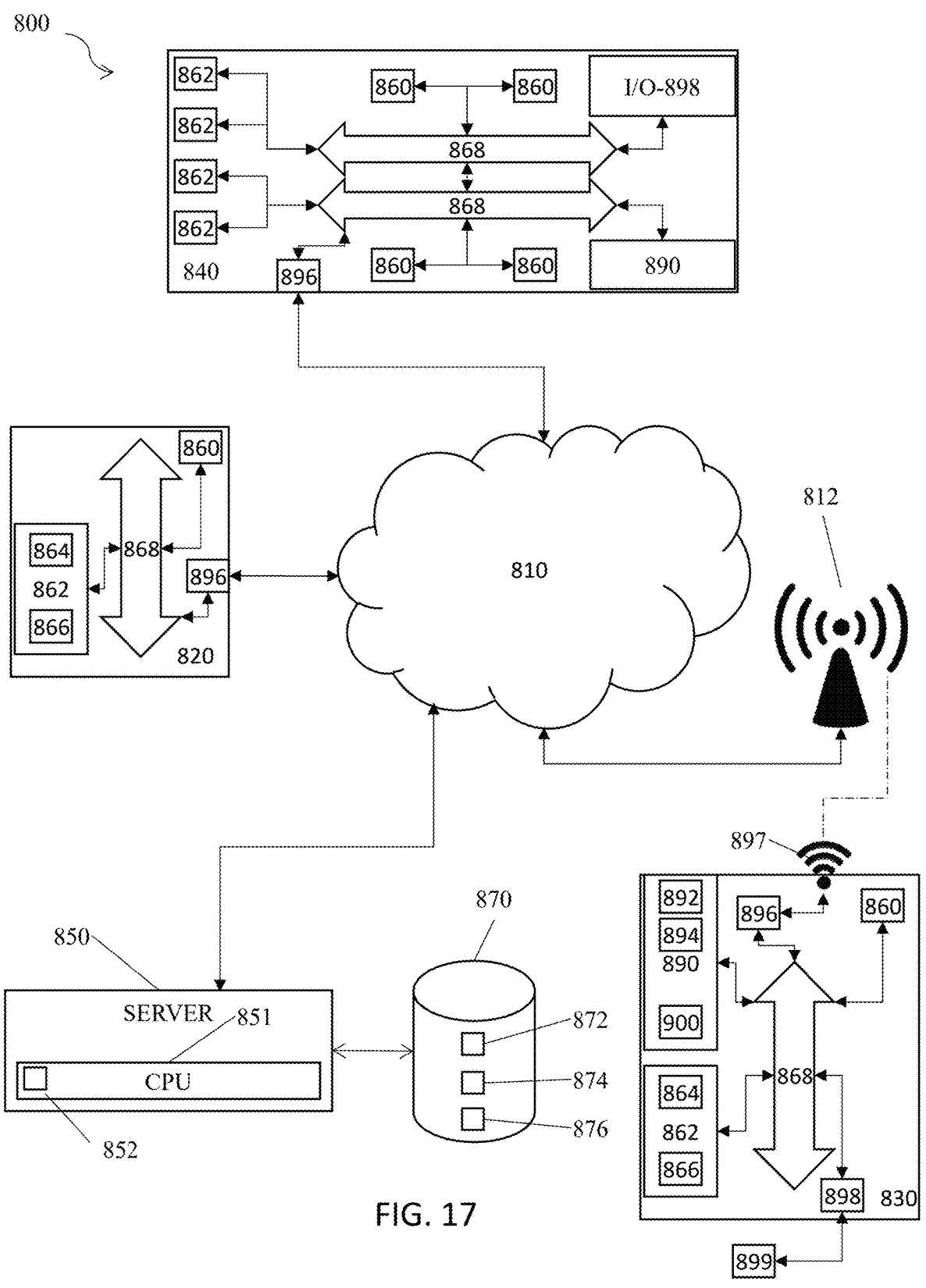
FIG. 17 is a schematic diagram of a system of the present invention.

FIG. 17 is a schematic diagram of an embodiment of the invention illustrating a computer system, generally described as 800, having a network 810, a plurality of computing devices 820, 830, 840, a server 850, and a database 870.

The server 850 is constructed, configured, and coupled to enable communication over a network 810 with a plurality of computing devices 820, 830, 840. The server 850 includes a processing unit 851 with an operating system 852. The operating system 852 enables the server 850 to communicate through network 810 with the remote, distributed user devices. Database 870 is operable to house an operating system 872, memory 874, and programs 876.

In one embodiment of the invention, the system 800 includes a network 810 for distributed communication via a wireless communication antenna 812 and processing by at least one mobile communication computing device 830. Alternatively, wireless and wired communication and connectivity between devices and components described herein include wireless network communication such as WI-FI, WORLDWIDE INTEROPERABILITY FOR MICRO-WAVE ACCESS (WIMAX), Radio Frequency (RF) communication including RF identification (RFID), NEAR FIELD COMMUNICATION (NFC), BLUETOOTH including BLUETOOTH LOW ENERGY (BLE), ZIGBEE, Infrared (IR) communication, cellular communication, satellite communication, Universal Serial Bus (USB), Ethernet communications, communication via fiber-optic cables, coaxial cables, twisted pair cables, and/or any other type of wireless or wired communication. In another embodiment of the invention, the system 800 is a virtualized computing system capable of executing any or all aspects of software and/or application components presented herein on the computing devices 820, 830, 840. In certain aspects, the computer system 800 is operable to be implemented using hardware or a combination of software and hardware, either in a dedicated computing device, or integrated into another entity, or distributed across multiple entities or computing devices.

By way of example, and not limitation, the computing devices 820, 830, 840 are intended to represent various forms of electronic devices including at least a processor and a memory, such as a server, blade server, mainframe, mobile phone, personal digital assistant (PDA), smartphone, desktop computer, netbook computer, tablet computer, workstation, laptop, and other similar computing devices. The components shown here, their connections and relationships, and their functions, are meant to be exemplary only, and are not meant to limit implementations of the invention described and/or claimed in the present application.

In one embodiment, the computing device 820 includes components such as a processor 860, a system memory 862 having a random access memory (RAM) 864 and a read-only memory (ROM) 866, and a system bus 868 that couples the memory 862 to the processor 860. In another embodiment, the computing device 830 is operable to additionally include components such as a storage device 890 for storing the operating system 892 and one or more application programs 894, a network interface unit 896, and/or an input/output controller 898. Each of the components is operable to be coupled to each other through at least one bus 868. The input/output controller 898 is operable to receive and process input from, or provide output to, a number of other devices 899, including, but not limited to, alphanumeric input devices, mice, electronic styluses, display units, touch screens, gaming controllers, joy sticks, touch pads, signal generation devices (e.g., speakers), augmented reality/virtual reality (AR/VR) devices (e.g., AR/VR headsets), or printers.

By way of example, and not limitation, the processor 860 is operable to be a general-purpose microprocessor (e.g., a central processing unit (CPU)), a graphics processing unit (GPU), a microcontroller, a Digital Signal Processor (DSP), an Application Specific Integrated Circuit (ASIC), a Field Programmable Gate Array (FPGA), a Programmable Logic Device (PLD), a controller, a state machine, gated or transistor logic, discrete hardware components, or any other suitable entity or combinations thereof that can perform calculations, process instructions for execution, and/or other manipulations of information.

In another implementation, shown as 840 in FIG. 17, multiple processors 860 and/or multiple buses 868 are operable to be used, as appropriate, along with multiple memories 862 of multiple types (e.g., a combination of a DSP and a microprocessor, a plurality of microprocessors, one or more microprocessors in conjunction with a DSP core).

Also, multiple computing devices are operable to be connected, with each device providing portions of the necessary operations (e.g., a server bank, a group of blade servers, or a multi-processor system). Alternatively, some steps or methods are operable to be performed by circuitry that is specific to a given function.

According to various embodiments, the computer system 800 is operable to operate in a networked environment using logical connections to local and/or remote computing devices 820, 830, 840 through a network 810. A computing device 830 is operable to connect to a network 810 through a network interface unit 896 connected to a bus 868. Computing devices are operable to communicate communication media through wired networks, direct-wired connections or wirelessly, such as acoustic, RF, or infrared, through an antenna 897 in communication with the network antenna 812 and the network interface unit 896, which are operable to include digital signal processing circuitry when necessary. The network interface unit 896 is operable to provide for communications under various modes or protocols.

In one or more exemplary aspects, the instructions are operable to be implemented in hardware, software, firmware, or any combinations thereof. A computer readable medium is operable to provide volatile or non-volatile storage for one or more sets of instructions, such as operating systems, data structures, program modules, applications, or other data embodying any one or more of the methodologies or functions described herein. The computer readable medium is operable to include the memory 862, the processor 860, and/or the storage media 890 and is operable be a single medium or multiple media (e.g., a centralized or distributed computer system) that store the one or more sets of instructions 900. Non-transitory computer readable media includes all computer readable media, with the sole exception being a transitory, propagating signal per se. The instructions 900 are further operable to be transmitted or received over the network 810 via the network interface unit 896 as communication media, which is operable to include a modulated data signal such as a carrier wave or other transport mechanism and includes any delivery media. The term "modulated data signal" means a signal that has one or more of its characteristics changed or set in a manner as to encode information in the signal.

Storage devices 890 and memory 862 include, but are not limited to, volatile and non-volatile media such as cache, RAM, ROM, EPROM, EEPROM, FLASH memory, or other solid state memory technology; discs (e.g., digital versatile discs (DVD), HD-DVD, BLU-RAY, compact disc (CD), or CD-ROM) or other optical storage; magnetic cassettes, magnetic tape, magnetic disk storage, floppy disks, or other magnetic storage devices; or any other medium that can be used to store the computer readable instructions and which can be accessed by the computer system 800.

In one embodiment, the computer system 800 is within a cloud-based network. In one embodiment, the server 850 is a designated physical server for distributed computing devices 820, 830, and 840. In one embodiment, the server 850 is a cloud-based server platform. In one embodiment, the cloud-based server platform hosts serverless functions for distributed computing devices 820, 830, and 840.

In another embodiment, the computer system 800 is within an edge computing network. The server 850 is an edge server, and the database 870 is an edge database. The edge server 850 and the edge database 870 are part of an edge computing platform. In one embodiment, the edge server 850 and the edge database 870 are designated to distributed computing devices 820, 830, and 840. In one embodiment, the edge server 850 and the edge database 870 are not designated for distributed computing devices 820, 830, and 840. The distributed computing devices 820, 830, and 840 connect to an edge server in the edge computing network based on proximity, availability, latency, bandwidth, and/or other factors.

It is also contemplated that the computer system 800 is operable to not include all of the components shown in FIG. 17, is operable to include other components that are not explicitly shown in FIG. 17, or is operable to utilize an architecture completely different than that shown in FIG. 17. The various illustrative logical blocks, modules, elements, circuits, and algorithms described in connection with the embodiments disclosed herein are operable to be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application (e.g., arranged in a different order or partitioned in a different way), but such implementation decisions should not be interpreted as causing a departure from the scope of the present invention.

Certain modifications and improvements will occur to those skilled in the art upon a reading of the foregoing description. The above-mentioned examples are provided to serve the purpose of clarifying the aspects of the invention and it will be apparent to one skilled in the art that they do not serve to limit the scope of the invention. All modifications and improvements have been deleted herein for the sake of conciseness and readability but are properly within the scope of the present invention.

The invention claimed is:
1. An artificial intelligence (AI)-based system for automatically identifying molecules in an analyte, comprising:
   one or more servers configured to receive training data from one or more spectrometers or chemical analysis devices;
   at least one reactor; and
   an AI module on the one or more servers;

wherein the training data corresponds with training samples of varying concentrations each comprising at least one of a plurality of known elements and/or compounds;
   wherein the AI module generates a plurality of correlation coefficients, wherein the correlation coefficients correlate emission intensity and concentration of the training samples;
   wherein the AI module is operable to develop characteristic profiles for the plurality of known elements and/or compounds by training the AI module on portions of the training data identified by the plurality of correlation coefficients;
   wherein the at least one reactor is operable to generate plasma from the analyte;
   wherein the one or more servers receives experimental data for the plasma from a testing spectrometer; and
   wherein the AI module automatically generates a report with indications and concentrations of present identified molecules based on comparison of the experimental data to the characteristic profiles.

2. The system of claim 1, wherein the one or more servers include cloud servers, and wherein the training data received from the one or more spectrometers or chemical analysis devices is combined with public datasets and/or additional third party datasets.

3. The system of claim 1, wherein the one or more spectrometers or chemical analysis devices comprises an optical emission spectroscopy (OES) spectrometer.

4. The system of claim 1, wherein the AI module is operable to divide spectrum graphs of the training samples into a plurality of wavelength bins, wherein the AI module is operable to generate a correlation coefficient for each of the plurality of wavelength bins.

5. The system of claim 1, wherein the training data is obtained with varying integration time, reactor chamber pressure, and/or wavelength and/or intensity of light from the one or more spectrometers or chemical analysis devices.

6. The system of claim 1, wherein the AI module calculates at least one correlation function of emission intensity and concentration for each of the training samples.

7. The system of claim 1, wherein the AI module includes one or more machine learning (ML) models, deep learning (DL) models, neural networks (NNs), support vector machines (SVMs), and/or transformers.

8. The system of claim 1, wherein the AI module is operable to adjust integration time, spectral resolution, and/or entrance slit width of the testing spectrometer based on noise and/or saturation in the experimental data.

9. An artificial intelligence (AI)-based method for automatically identifying molecules in an analyte, comprising:
   receiving training data via one or more servers from one or more spectrometers or chemical analysis devices;
   wherein the training data comprises a plurality of measured spectral graphs corresponding with training samples of varying concentrations each comprising at least one of a plurality of known elements and/or compounds;
   generating correlation coefficients for the plurality of measured spectral graphs via an AI module on the one or more servers, wherein the correlation coefficients correlate emission intensity and the concentrations of the training samples;
   automatically developing characteristic profiles for the plurality of known elements and/or compounds by training the AI module on portions of the training data identified by the plurality of correlation coefficients;

generating plasma from the analyte using at least one reactor;

receiving experimental data for the plasma from a testing spectrometer via the one or more servers; and automatically generating a report with indications and concentrations of present identified molecules based on comparison of the experimental data to the characteristic profiles using the AI module.

10. The method of claim 9, wherein the one or more servers include cloud servers, and further comprising combining the training data received from the one or more spectrometers or chemical analysis devices with public datasets and/or additional third party datasets.

11. The method of claim 9, wherein the one or more spectrometers or chemical analysis devices comprises an optical emission spectroscopy (OES) spectrometer.

12. The method of claim 9, further comprising calibrating the measured spectral graphs against known reference lines and/or normalizing the measured spectral graphs by total emission intensity or an internal reference line via the AI module.

13. The method of claim 9, further comprising dividing the measured spectral graphs into a plurality of wavelength bins and generating a correlation coefficient for each of the wavelength bins using the AI module.

14. The method of claim 13, wherein the portions of the training data are one or more of the plurality of wavelength bins having an absolute value of a correlation coefficient above a threshold.

15. The method of claim 9, further comprising varying integration time of the one or more spectrometers or chemical analysis devices, pressure of the reactor, and/or wavelength and/or intensity of the light of the one or more spectrometers or chemical analysis devices for each of the plurality of measured spectral graphs.

16. The method of claim 9, further comprising regenerating the report using the AI module when the characteristic profiles are updated.

17. An artificial intelligence (AI)-based system for automatically identifying molecules in an analyte, comprising:

one or more cloud servers configured to receive training data from one or more spectrometers or chemical analysis devices;

at least one reactor; and an AI module on the one or more cloud servers;

wherein the training data corresponds with training samples of varying concentrations each comprising at least one of a plurality of known elements and/or compounds;

wherein the training data received from the one or more spectrometers or chemical analysis devices is stored on the one or more cloud servers;

wherein the AI module is operable to develop characteristic profiles for the plurality of known elements and/or compounds by training the AI module on portions of the training data identified by a plurality of coefficients which correlate emission intensity and concentration of the training samples;

wherein the at least one reactor is operable to generate plasma from the analyte;

wherein the one or more cloud servers receive experimental data for the plasma from a testing spectrometer;

wherein the AI module automatically generates a report with indications of present identified molecules based on comparison of the experimental data to the characteristic profiles;

wherein the AI module automatically generates updated characteristic profiles based on a combination of the stored training data and new training data; and wherein the AI module automatically generates an updated report when the updated characteristic profiles are generated.

18. The system of claim 17, wherein the training data is combined with public datasets and/or additional third party datasets.

19. The system of claim 17, wherein the training data is geotagged based on a geographic location of the one or more spectrometers or chemical analysis devices.

20. The system of claim 17, wherein the one or more spectrometers or chemical analysis devices comprises an optical emission spectroscopy (OES) spectrometer.

\* \* \* \* \*